United States Patent
Bachmaier et al.

(10) Patent No.: US 12,357,298 B2
(45) Date of Patent: *Jul. 15, 2025

(54) SURGICAL FIXATION SYSTEMS AND METHODS

(71) Applicant: ARTHREX, INC., Naples, FL (US)

(72) Inventors: Samuel Bachmaier, Mauern (DE); Coen Wijdicks, Munich (DE); Stefan Krupp, Munich (DE); Adrian Wilson, Basingstoke (GB); Patrick Smith, Columbia, MO (US); Jacob Jolly, Naples, FL (US)

(73) Assignee: ARTHREX, INC., Naples, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/663,178

(22) Filed: May 14, 2024

(65) Prior Publication Data
US 2024/0299023 A1 Sep. 12, 2024

Related U.S. Application Data

(63) Continuation of application No. 17/878,129, filed on Aug. 1, 2022, now Pat. No. 12,011,156, and a (Continued)

(51) Int. Cl.
*A61B 17/04* (2006.01)
*A61B 17/86* (2006.01)
(Continued)

(52) U.S. Cl.
CPC ...... *A61B 17/0401* (2013.01); *A61B 17/8645* (2013.01); *A61F 2/0811* (2013.01);
(Continued)

(58) Field of Classification Search
CPC ........ A61B 17/0401; A61B 2017/0404; A61B 2017/0406; A61F 2/0811; A61F 2002/0852; A61F 2002/0882
See application file for complete search history.

(56) References Cited

U.S. PATENT DOCUMENTS

| 5,306,301 A * | 4/1994 | Graf ................. A61F 2/0805 623/13.12 |
| 6,267,767 B1 | 7/2001 | Strobel et al. |

(Continued)

FOREIGN PATENT DOCUMENTS

| EP | 2238944 | 10/2010 |
| EP | 2455040 | 5/2012 |
| WO | 2016090104 | 6/2016 |

OTHER PUBLICATIONS

Hamido, F, et al., "The use of the LARS artificial ligament to augment a short or undersized ACL hamstrings tendon graft," Knee (2010), doi:10.1016/j.knee.2010.09.003.
(Continued)

*Primary Examiner* — Matthew J Lawson
(74) *Attorney, Agent, or Firm* — Carlson, Gaskey & Olds, P.C.

(57) ABSTRACT

A surgical fixation system can include a fixation device, a loop connected to the fixation device, a graft carried by the loop, and a reinforcement material. Surgical fixation systems can be used in various tissue reconstruction procedures, including but not limited to, ACL and PCL reconstructions. The graft and the reinforcement material may be tensioned independently of one another to avoid stress shielding the graft.

20 Claims, 28 Drawing Sheets

Related U.S. Application Data continuation of application No. 16/655,298, filed on Oct. 17, 2019, now Pat. No. 11,432,813, which is a continuation of application No. 15/686,469, filed on Aug. 25, 2017, now Pat. No. 10,448,945.

(60) Provisional application No. 62/470,573, filed on Mar. 13, 2017, provisional application No. 62/379,370, filed on Aug. 25, 2016.

(51) Int. Cl.
*A61F 2/08* (2006.01)
*A61B 17/06* (2006.01)

(52) U.S. Cl.
CPC . *A61B 2017/0404* (2013.01); *A61B 17/06109* (2013.01); *A61F 2002/0852* (2013.01); *A61F 2002/0882* (2013.01)

(56) References Cited

U.S. PATENT DOCUMENTS

| | | | |
|---|---|---|---|
| 6,517,578 | B2 | 2/2003 | Hein |
| 6,833,005 | B1 | 12/2004 | Mantas et al. |
| 8,226,715 | B2 | 7/2012 | Hwang et al. |
| 8,439,976 | B2 | 5/2013 | Albertorio et al. |
| 8,460,379 | B2 | 6/2013 | Albertorio et al. |
| 8,470,037 | B2 | 6/2013 | Re et al. |
| 8,771,316 | B2 | 7/2014 | Denham et al. |
| 8,852,250 | B2 | 10/2014 | Lombardo et al. |
| 9,168,124 | B2 | 10/2015 | Guerra et al. |
| 9,357,990 | B2 | 6/2016 | Ferguson et al. |
| 9,561,027 | B2 | 2/2017 | Perriello et al. |
| 9,974,643 | B2 | 5/2018 | Sengun et al. |
| 10,405,968 | B2 | 9/2019 | Gustafson et al. |
| 2001/0041938 | A1 | 11/2001 | Hein |
| 2002/0161275 | A1 | 10/2002 | Schweich, Jr. et al. |
| 2005/0187577 | A1 | 8/2005 | Selvitelli et al. |
| 2009/0182335 | A1 | 7/2009 | Struhl |
| 2010/0256677 | A1 | 10/2010 | Albertorio et al. |
| 2010/0268273 | A1 | 10/2010 | Albertorio et al. |
| 2010/0324676 | A1 | 12/2010 | Albertorio et al. |
| 2012/0046693 | A1 | 2/2012 | Denham et al. |
| 2013/0096612 | A1* | 4/2013 | Zajac ................ A61B 17/0469 606/232 |
| 2013/0197580 | A1 | 8/2013 | Perriello et al. |
| 2013/0268000 | A1 | 10/2013 | Harner et al. |
| 2013/0289574 | A1 | 10/2013 | Shinde |
| 2014/0155937 | A1 | 6/2014 | Shinde |
| 2014/0257346 | A1 | 9/2014 | Sengun et al. |
| 2015/0057750 | A1 | 2/2015 | Timmerman |
| 2015/0094762 | A1 | 4/2015 | Spenciner |
| 2015/0157449 | A1 | 6/2015 | Gustafson et al. |
| 2015/0297338 | A1 | 10/2015 | Ammann |
| 2016/0157851 | A1 | 6/2016 | Spenciner |
| 2016/0354195 | A1 | 12/2016 | Spenciner |
| 2017/0360437 | A1 | 12/2017 | Ferguson et al. |
| 2019/0223858 | A1 | 7/2019 | Zajac et al. |

OTHER PUBLICATIONS

Nancoo, T, et al., "TransMedial All-Inside Posterior Cruciate Ligament Reconstruction Using a Reinforced Tibial Inlay Graft," Arthroscopy Techniques, vol. 2, No. 4 (Nov.), 2013: pp. e381-e388.

The International Search Report and Written Opinion for PCT Application No. PCT/US2017/048579, mailed Nov. 28, 2017.

Written Opinion of the International Preliminary Examining Authority for PCT Application No. PCT/US2017/048579, dated Aug. 27, 2018.

International Preliminary Report on Patentability for PCT Application No. PCT/US2017/048579, dated Nov. 23, 2018.

Translation of Notice of Reasons for Rejection, Japanese Patent Application No. 2019-510600 dated Oct. 13, 2020.

* cited by examiner

Surgical Fixation with System 210

Fixation Steps:

1. Femoral Graft Insertion
2. Tibial Graft Insertion
3. Tape Fixation in Full Extension with SL
4. Tibial Screw Fixation in Full Extension
5. Precycles Over Full Flexion Range (10x)
   - Picture Not Shown
6. Femoral Graft Retensioning
   - Picture Not Shown

SURGICAL FIXATION SYSTEMS AND METHODS

CROSS-REFERENCE TO RELATED APPLICATIONS

This is a continuation of U.S. patent application Ser. No. 17/878,129, filed Aug. 1, 2022, which is a continuation of U.S. patent application Ser. No. 16/655,298, filed Oct. 17, 2019, now U.S. Pat. No. 11,432,813, which is a continuation of U.S. patent application Ser. No. 15/686,469, filed Aug. 25, 2017, now U.S. Pat. No. 10,448,945, which claims the benefit of U.S. Provisional Application No. 62/379,370, filed Aug. 25, 2016 and U.S. Provisional Application No. 62/470,573, filed Mar. 13, 2017, the entire disclosures of which are incorporated by reference herein.

BACKGROUND

This disclosure relates to surgical fixation systems and methods for fixating a graft within a bone tunnel.

Tissue reconstruction surgeries, such as anterior cruciate ligament (ACL) reconstructions and posterior cruciate ligament (PCL) reconstructions, typically involve drilling a tunnel through bone, positioning a substitute graft into the bone tunnel, and fixating the graft within the bone tunnel using a fixation device, such as a button, a screw, or the like. The substitute graft may be reinforced by adding a reinforcement material to the surgical fixation system.

SUMMARY

This disclosure relates to surgical fixation systems and methods. The surgical fixation systems include a fixation device, a loop connected to the fixation device, a graft carried by the loop, and a reinforcement material. The surgical fixation system can be used in various tissue reconstruction procedures, including but not limited to, ACL and PCL reconstructions.

A surgical method according to an exemplary aspect of this disclosure includes, inter alia, fixating a graft within a bone tunnel using a surgical fixation system. A surgical fixation system can include a button, a loop connected to the button, and a reinforcement material connected to the button but unattached to a graft. The method can further include tensioning a graft and a reinforcement material separately from one another, resulting in independent tensioning.

A surgical method according to another exemplary aspect of this disclosure includes, inter alia, fixating a graft within a bone tunnel using a surgical fixation system that includes a button, a loop connected to the button, and a reinforcement material connected to the button but unattached to the graft, tensioning the graft at a first tension such that the graft reacts to joint strain loads up to a predefined strain threshold, and tensioning the reinforcement material at a second, independent tension such that the reinforcement material only reacts to the joint strain loads that exceed the predefined strain threshold.

A surgical fixation system according to an exemplary aspect of this disclosure includes, inter alia, a fixation device, a loop connected to the fixation device, a graft carried by the loop, and a reinforcement material connected to the button and unattached to either the graft or the adjustable loop. The reinforcement material is tensionable separately from the graft.

BRIEF DESCRIPTION OF THE DRAWINGS

The drawings that accompany the detailed description can be briefly described as follows.

DETAILED DESCRIPTION

Figure 1:
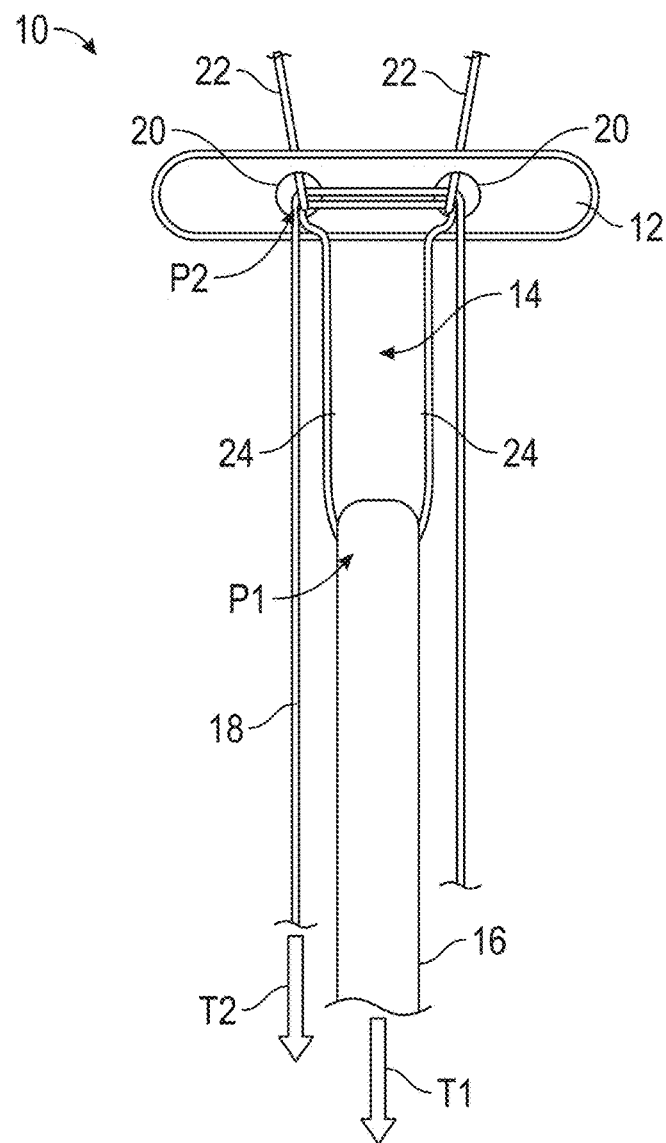
FIG. 1 illustrates a surgical fixation system for performing a tissue reconstruction procedure.

This disclosure relates to surgical fixation systems and methods. A surgical fixation system can include a fixation device, a loop connected to the fixation device, a graft carried by the loop, and a reinforcement material. Surgical fixation systems can be used in various tissue reconstruction procedures, including but not limited to, ACL and PCL reconstructions.

A surgical method according to an exemplary aspect of this disclosure includes, inter alia, fixating a graft within a bone tunnel using a surgical fixation system, and tensioning the graft and a reinforcement material of the surgical fixation system separately from one another, resulting in independent tensioning.

In a further embodiment, a surgical fixation system includes a button, a fixed or adjustable loop connected to the button, and a reinforcement material connected to the button but unattached to a graft.

In a further embodiment, an adjustable loop includes a first adjustable eyesplice and a second adjustable eyesplice interconnected with the first adjustable eyesplice.

In a further embodiment, a graft is connected to a loop.

In a further embodiment, a graft is looped over a loop and reinforcement material is passed through apertures of a button.

In a further embodiment, tensioning occurs after fixating.

In a further embodiment, joint strain loads up to a predefined strain threshold are reacted with a graft, and joint strain loads that exceed a predefined strain threshold are reacted with reinforcement material.

In a further embodiment, a different amount of slack is left in a reinforcement material compared to a graft.

In a further embodiment, a greater amount of slack is left in reinforcement material than in a graft.

In a further embodiment, a different amount of tension is left in a reinforcement material compared to a graft.

In a further embodiment, a lesser amount of tension is left in a reinforcement material compared to a graft.

In a further embodiment, a graft and a reinforcement material are fixated relative to a first bone with a button, the graft is fixated relative to a second bone with a first screw or a first suture anchor, and the reinforcement material is fixated relative to the second bone with a second screw or a second suture anchor.

In a further embodiment, a second screw or a second suture anchor is positioned within a separate bone hole from a first screw or a first suture anchor.

A surgical method according to another exemplary aspect of this disclosure includes, inter alia, fixating a graft within a bone tunnel using a surgical fixation system that includes a button, a loop connected to the button, and a reinforcement material connected to the button but unattached to a graft, tensioning the graft at a first tension such that the graft reacts to joint strain loads up to a predefined strain threshold, and tensioning the reinforcement material at a second tension such that the reinforcement material only reacts to the joint strain loads that exceed the predefined strain threshold.

In a further embodiment, a different amount of slack is left in a reinforcement material compared to a graft.

In a further embodiment, a greater amount of slack is left in a reinforcement material than in a graft.

In a further embodiment, a different amount of tension is left in a reinforcement material compared to a graft.

In a further embodiment, a lesser amount of tension is left in a reinforcement material compared to a graft.

In a further embodiment, a graft and a reinforcement material are fixated relative to a first bone with a button, the graft is fixated relative to a second bone with a first screw or a first suture anchor, and the reinforcement material is fixated relative to the second bone with a second screw or a second suture anchor.

In a further embodiment, a graft and a reinforcement material are fixated relative to a first bone with a button and are fixated relative to a second bone with a second button.

A surgical fixation system according to an exemplary aspect of this disclosure includes, inter alia, a fixation device, a loop connected to the fixation device, a graft carried by the loop, and a reinforcement material connected to the button and unattached to either the graft or the adjustable loop. The reinforcement material is tensionable separately from the graft, resulting in independent tensioning.

FIG. 1 illustrates an exemplary surgical fixation system 10. The surgical fixation system 10 may be used to perform a variety of tissue reconstruction procedures. The tissue reconstruction procedures could include any procedure in which it is desirable to position a replacement graft within a bone tunnel to repair torn tissue. ACL and PCL reconstructions are but two non-limiting examples of reconstruction procedures which could benefit from the use of the surgical fixation system 10 of this disclosure.

The surgical fixation system 10 includes a fixation device 12, a loop 14, a graft 16, and a reinforcement material 18. The fixation device 12 provides cortical bone fixation of the graft 16 after the graft 16 has been positioned within a bone tunnel. In an embodiment, the fixation device 12 is a button. However, fixation devices having other similar configurations could also be used. The fixation device 12 may be oblong or round and may be made of either metallic or polymeric materials within the scope of this disclosure.

In another embodiment, the fixation device 12 includes one or more apertures 20 formed through the body of the fixation device 12 for receiving the loop 14 and the reinforcement material 18. The fixation device 12 of the embodiment of FIG. 1, for example, includes two apertures 20 for connecting the loop 14 and the reinforcement material 18 to the fixation device 12. Although not shown, the fixation device 12 could include additional apertures or openings in excess of two.

The loop 14 may be a fixed loop or an adjustable loop. In a non-limiting embodiment, the loop 14 of the surgical fixation system 10 is a made of a flexible material and includes an adjustable length and perimeter. Free braid strands 22 of the loop 14 may be pulled to reduce the size of the loop 14. For example, the loop 14 may be adjusted in a first direction by pulling the free braid stands 22 but is prevented from loosening in the opposite direction due to applied internal tensile forces.

The loop 14 may include one or more adjustable eyesplices 24 that are formed by splicing the flexible material that is used to form the loop 14 through itself. The loop 14 is connected to the fixation device 12 prior to completely forming the loop 14. An exemplary method of forming the loop 14 and connecting it to the fixation device 12 is discussed in greater detail below with respect to FIGS. 2-8.

The graft 16 is connected at a first fixation location P1 of the surgical fixation system 10. In an exemplary embodiment, the graft 16 is connected to the loop 14, and thus, the first fixation location P1 is at a cradle of the loop 14. For example, the graft 16 may be looped over a portion of the loop 14. The graft 16 could include tissue, tendon, ligament, synthetic material, biologic material, bone, or any combinations of such materials.

The reinforcement material 18 may be a suture construct. For example, the reinforcement material 18 could include suture tape, such as FiberTape®, suture tape coated with collagen, suture with biological material or a collagen coated material, a collagen patch, a biological construct such as Arthroflex®, a superelastic material such as nitinol, or any other similar construct.

The reinforcement material 18 is connected at a second fixation location P2 of the surgical fixation system 10. The second fixation location P2 is a different location from the first fixation location P1. In an exemplary embodiment, the second fixation location P2 is at the fixation device 12. The size of the fixation device 12 can be adjusted to accommodate the addition of the reinforcement material 18. The reinforcement material 18 may be passed through the apertures 20 of the fixation device 12 to connect the reinforcement material 18 to the surgical fixation system 10. The reinforcement material 18 is thus unconnected in any way to the graft 16. The reinforcement material 18 may be used to augment a ligament repair procedure and acts as a reinforcement that supports the primary repair provided by the graft 16. The reinforcement material 18 may therefore be referred to as a "safety belt." In another embodiment, the reinforcement material 18 may be utilized for providing tactile feedback of deployment (e.g., flipping) of the fixation device 12 during implantation.

In another exemplary embodiment, the graft 16 and the reinforcement material 18 can be tensioned separately from one another, resulting in independent tension loads. This is possible because these components are connected at the separate fixation locations P1, P2, respectively, of the surgical fixation system 10. For example, a first tension T1 may be applied to the graft 16, whereas a second, different tension T2 may be applied to the reinforcement material 18 during implantation of the surgical fixation system 10. Tension can also be reapplied to the graft 16 after tensioning the reinforcement material 18. Accordingly, joint loads may be shared between the graft 16 and the reinforcement material 18, with the reinforcement material 18 acting as a dynamic joint stabilizer that shares loads with the graft 16 according to its relative initial tensioning. In a non-limiting embodiment, the reinforcement material reacts loads that exceed a predefined strained threshold of the graft 16.

Figure 2:
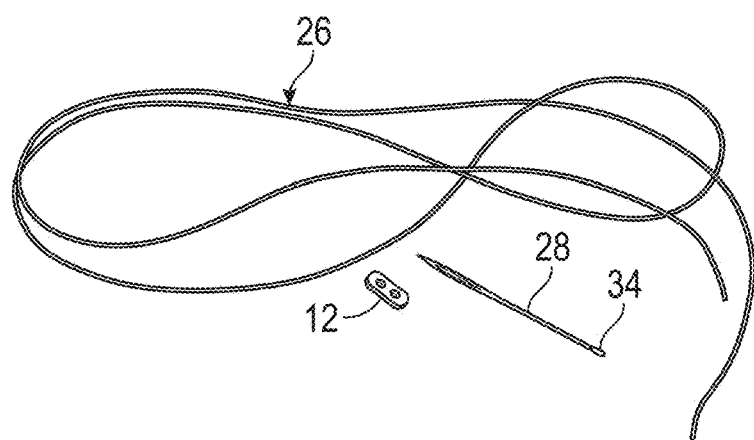
FIGS. 2, 3, 4, 5, 6, 7 and 8 schematically illustrate a method for forming an adjustable loop of the surgical fixation system of FIG. 1.

FIGS. 2-8 schematically illustrate an exemplary method of forming the loop 14 of the surgical fixation system 10 of FIG. 1. FIG. 2 illustrates starting materials for constructing the loop 14 and attaching it to the fixation device 12. The starting materials include a flexible strand 26, such as a suture strand, a suture passing device 28, such as a needle, and the fixation device 12, such as a button.

Figure 3:
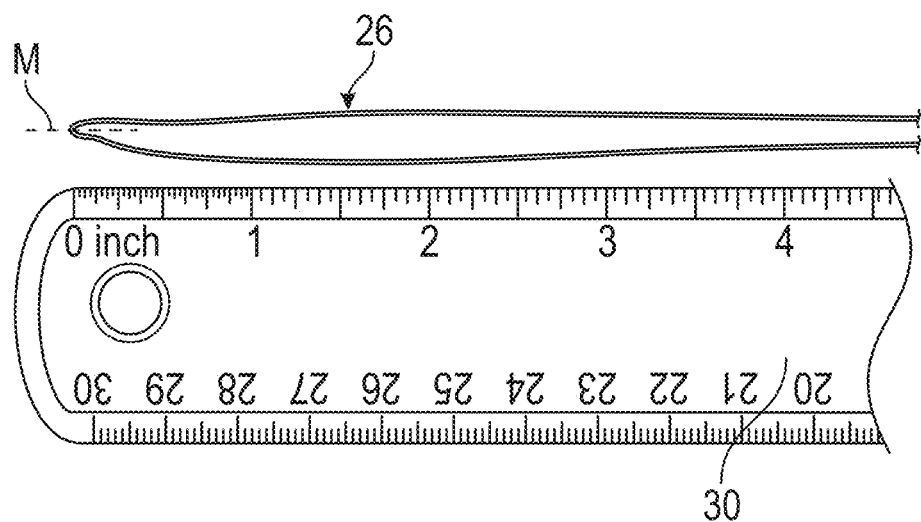

Referring next to FIG. 3, the flexible strand 26 is folded in half to create two substantially equal length and parallel braid strands. The flexible strand 26 may be folded near its midpoint M to create the two substantially equal length and parallel braid strands. A measuring device 30, such as a ruler, may be used to select a desired amount of the flexible strand 26 for creating a loop 14 having a desired size.

Figure 4:
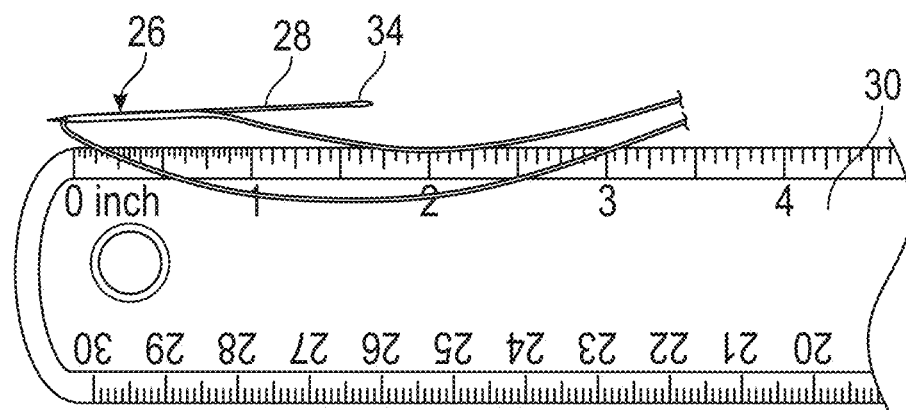
Figure 5:
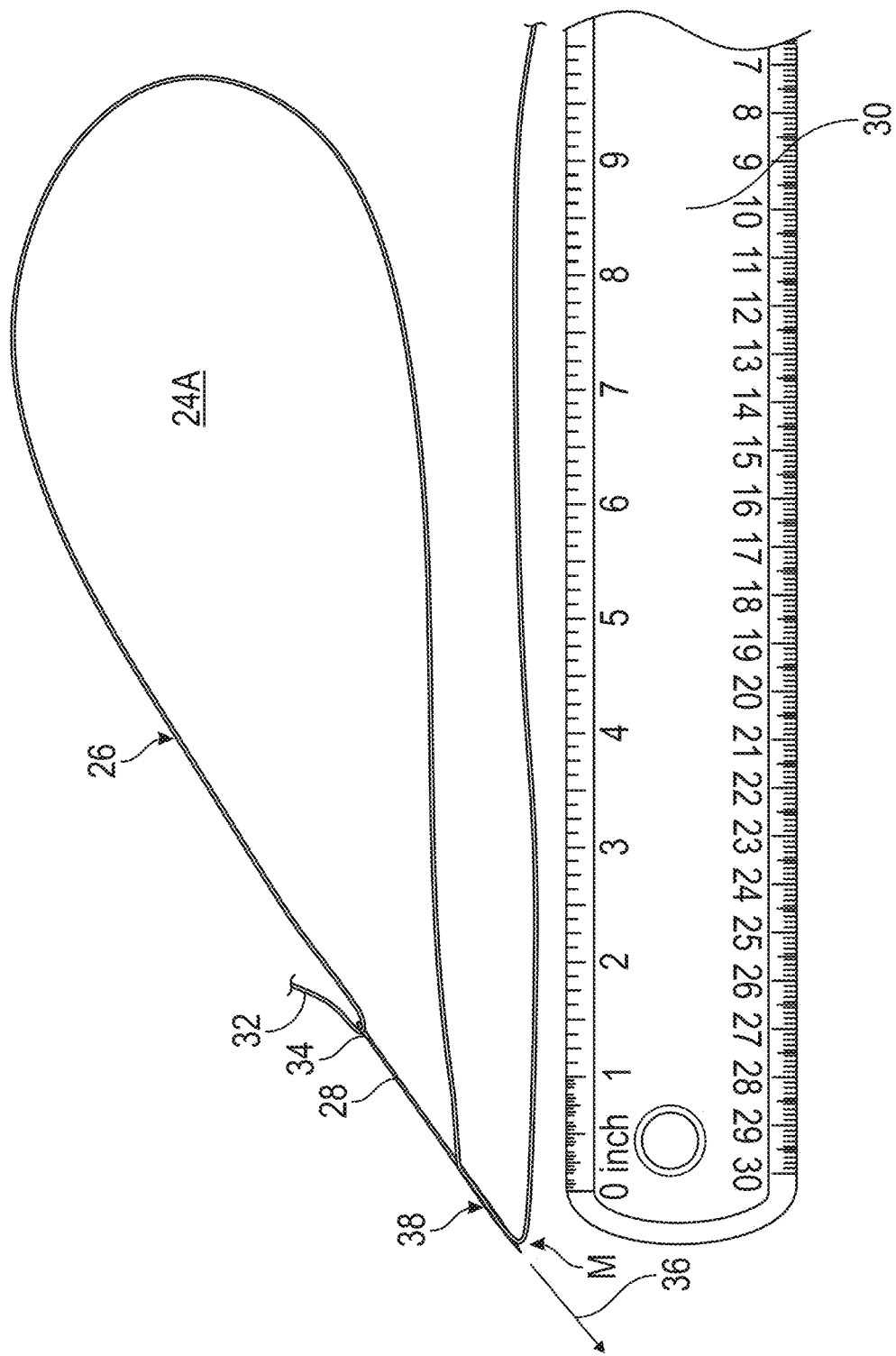

FIGS. 4 and 5 illustrate the formation of a first adjustable eyesplice 24A of the loop 14. The first adjustable eyesplice 24A is created by first passing the suture passing device 28 through the flexible strand 26 (see FIG. 4). The suture passing device 28 may be passed through the flexible strand 26 near the midpoint M where the flexible strand 26 was previously folded to mark the location where the flexible strand 26 will ultimately be spliced through itself. A first free end 32 of the flexible strand 26 is next inserted through an eyelet 34 of the suture passing device 28 (see FIG. 5). The suture passing device 28 is then moved (e.g., pulled) in a direction of arrow 36 to splice the first free end 32 back through the flexible strand 26 at the location where the suture passing device 28 previously passed through the flexible strand 26. This creates a first spliced section 38 in the flexible strand 26.

Figure 6:
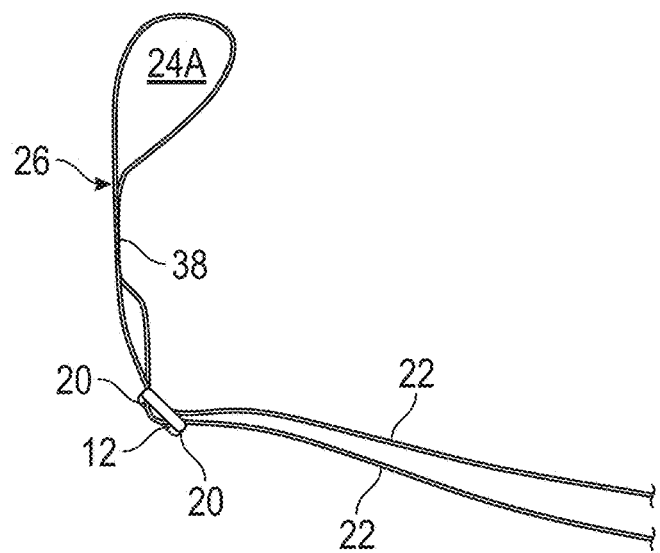

Referring now to FIG. 6, the free braid strands 22 of the flexible strand 26 are passed through the apertures 20 of the fixation device 12 to connect the flexible strand 26 to the fixation device 12. The fixation device 12 may be slid until it rests over the first spliced section 38.

Figure 7:
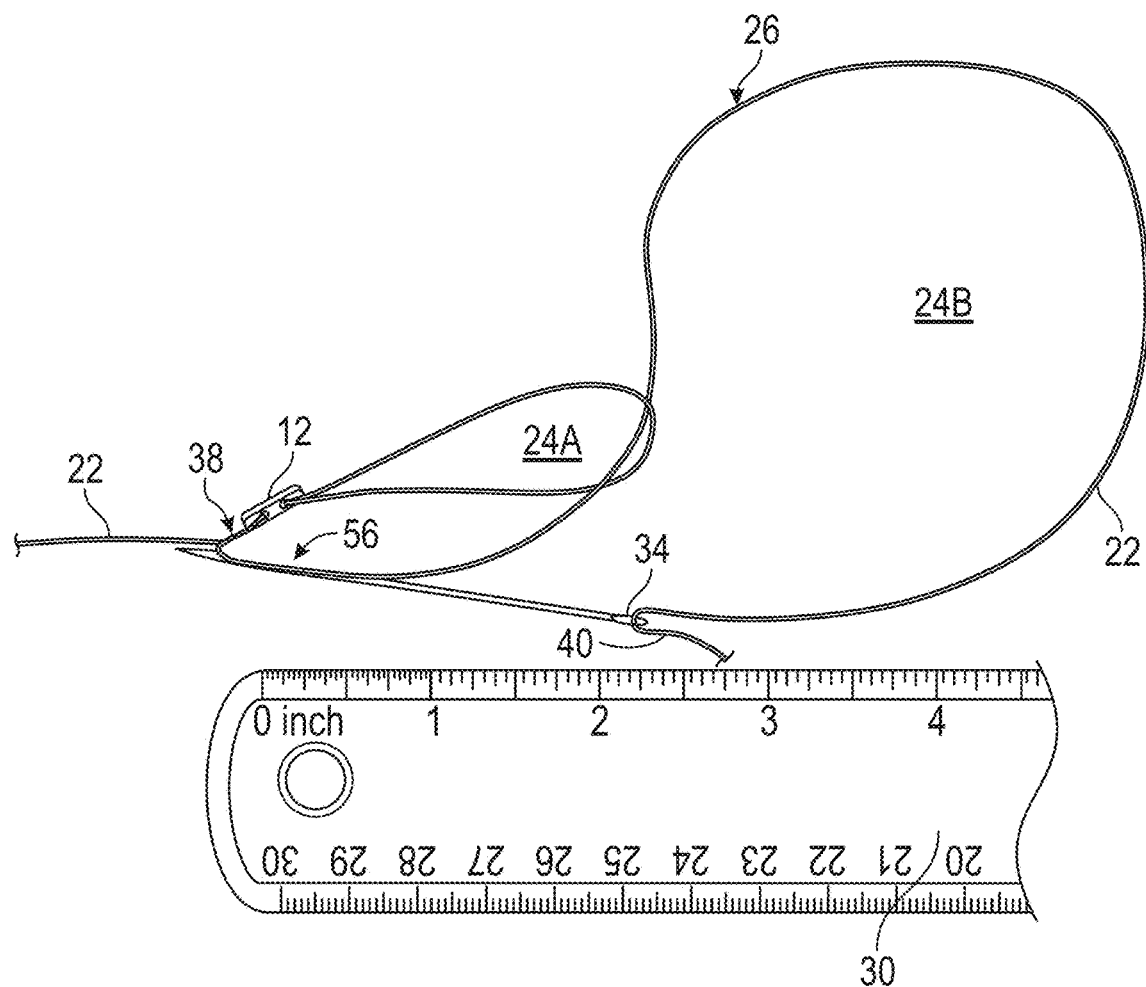

FIG. 7 illustrates the formation of a second adjustable eyesplice 24B of the loop 14. The second adjustable eyesplice 24B is created by passing the suture passing device 28 a second time through the flexible strand 26 at a location adjacent to the first spliced section 38. A second free end 40 of the flexible strand 26 is next looped through the first adjustable eyesplice 24A and inserted through the eyelet 34 of the suture passing device 28 prior to pulling the suture passing device 28 back through the flexible strand 26. This splices the second free end 40 back through the flexible strand 26 to create a second spliced section 56.

Figure 8:
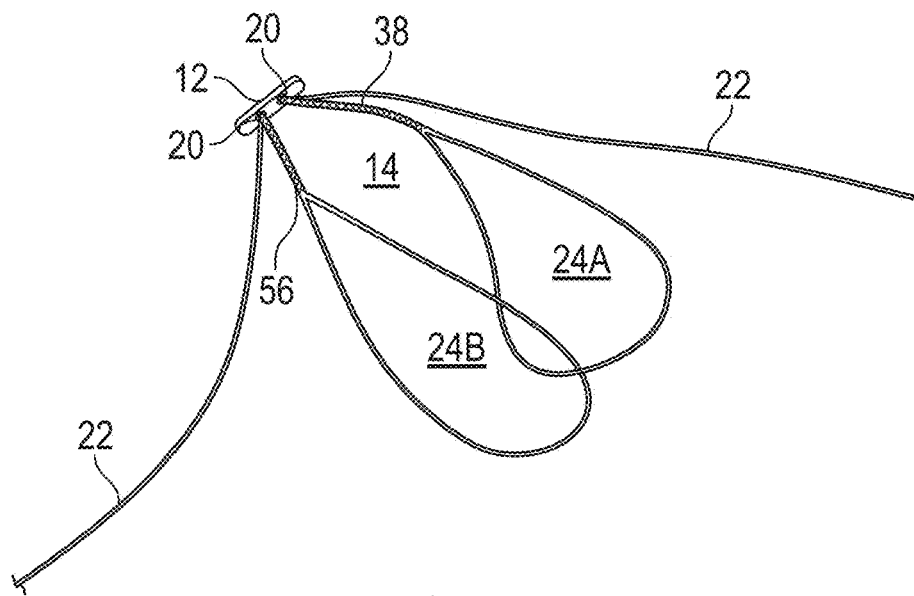

FIG. 8 illustrates the completed loop 14, which in this embodiment, includes two adjustable eyesplices 24A, 24B that are interconnected to one another. The fixation device 12 may be centered between the first adjustable eyesplice 24A and the second adjustable eyesplice 24B to complete the assembly procedure. The free braid strands 22 extending from the spliced sections 38, 56 may be positioned as desired within the apertures 20 of the fixation device 12. The free braid strands 22 may be pulled to constrict the size of the first and second adjustable eyesplices 24A, 24B and thus change the overall size of the loop 14.

Figure 9:
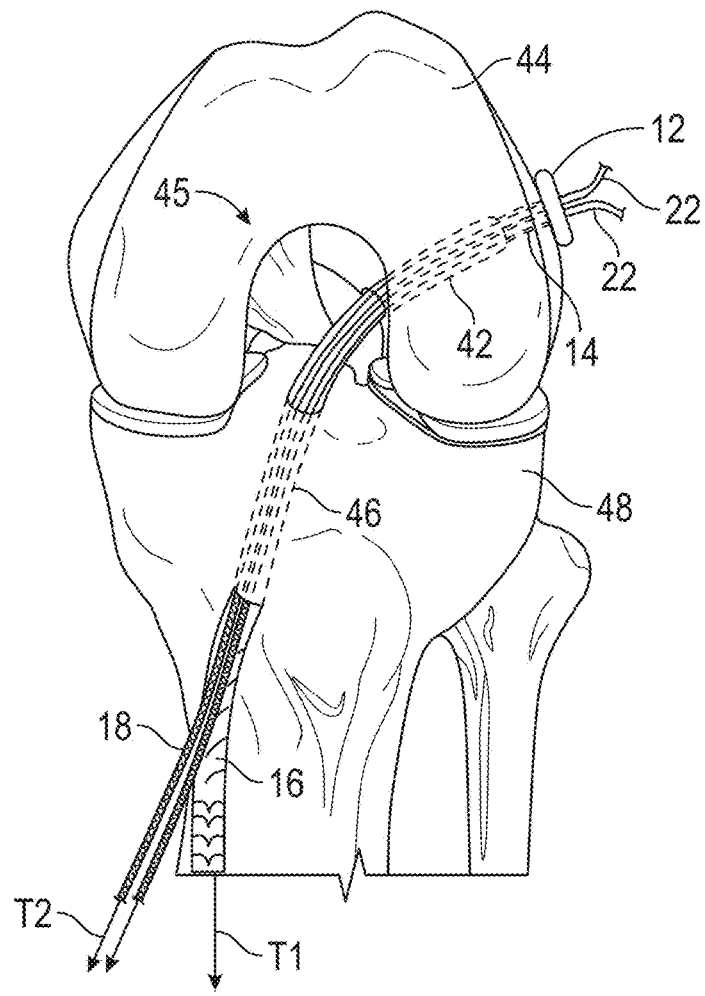
FIG. 9 schematically illustrates a use of the surgical fixation system of FIG. 1 as part of a tissue reconstruction procedure.

FIG. 9 illustrates an exemplary surgical use of the surgical fixation system 10 of FIG. 1 during a tissue reconstruction procedure, such as an ACL reconstruction procedure. However, it should be understood that this disclosure is not limited to ACL reconstruction procedures, and the surgical fixation system 10 could be used in a variety of reconstruction procedures within the scope of this disclosure.

The surgical fixation system 10 may be implanted within a joint 45 (e.g., a knee joint) to repair a torn tissue (e.g., a torn ACL). Prior to positioning the surgical fixation system 10 within the joint 45, a first bone tunnel 42 (e.g., a socket) is formed in a first bone 44 (e.g., a femur) and a second bone tunnel 46 (e.g., a passage) is formed in a second bone 48 (e.g., a tibia). The first bone tunnel 42 and the second bone tunnel 46 may be formed using known drilling techniques to establish voids within the first and second bones 44, 48 for accommodating the surgical fixation system 10.

In an exemplary embodiment, the surgical fixation system 10 is implanted by passing the fixation device 12 through the first bone tunnel 42 and the second bone tunnel 46. The fixation device 12 may be pulled through the first and second bone tunnels 42, 46 using a passing suture (not shown) and self-flips onto the cortex of the first bone 44 once tension is released on the passing suture.

After passing and flipping the fixation device 12, the loop 14 is positioned within the first bone tunnel 42. The free braid strands 22 may be pulled to adjust the size of the loop 14 and to aid the positioning of the loop 14 within the first bone tunnel 42. The loop 14 suspends the graft 16 within portions of the first bone tunnel 42 and the second bone tunnel 46, and the fixation device 12 suspends the reinforcement material 18 within portions of the first bone tunnel 42 and the second bone tunnel 46.

As shown in FIG. 9, both the graft 16 and the reinforcement material 18 may extend out of the second bone tunnel 46 and can be separately tensioned prior to completing the repair. For example, a first tension T1 may be applied to the graft 16, whereas a second, different tension T2 may be applied to the reinforcement material 18 since these components are unconnected to one another. The graft 16 can thus be retensioned after intraoperative preconditioning. Intraoperative preconditioning can be used to reduce residual laxity in the graft 16. Prior surgical fixation systems did not allow for separate tensioning of the graft 16 and reinforcement material 18, and therefore intraoperative preconditioning was not possible. Graft retensioning optimizes the mechanical stability of soft tissue by decreasing its dynamic elongation. An artificial material for augmentation (e.g., FiberTape®) provides an increased stiffness compared to soft tissue material, thus its resistance to dynamic elongation may be high enough without retensioning.

In addition, because the graft 16 and the reinforcement material 18 may be tensioned separately from one another, a different amount of slack can be provided in the reinforcement material 18 as compared to the graft 16 upon fixation at the second bone 48. In an exemplary embodiment, a greater amount of slack is left in the reinforcement material 18 as compared to the graft. In another exemplary embodiment, a different amount of tension is left in the reinforcement material 18 compared to the graft 16. In a further embodiment, a lesser amount of tension is left in the reinforcement material 18 compared to the graft 16. This creates a load sharing environment between the graft 16 and the reinforcement material 18 in which the graft 16 is configured to react to strain loads of the joint 45 up to a predefined strain threshold, and the reinforcement material 18 is configured to react to a portion of the strain loads that exceed the predefined strain threshold. In this way, the reinforcement material 18 does not stress shield the graft 16.

Figure 10:
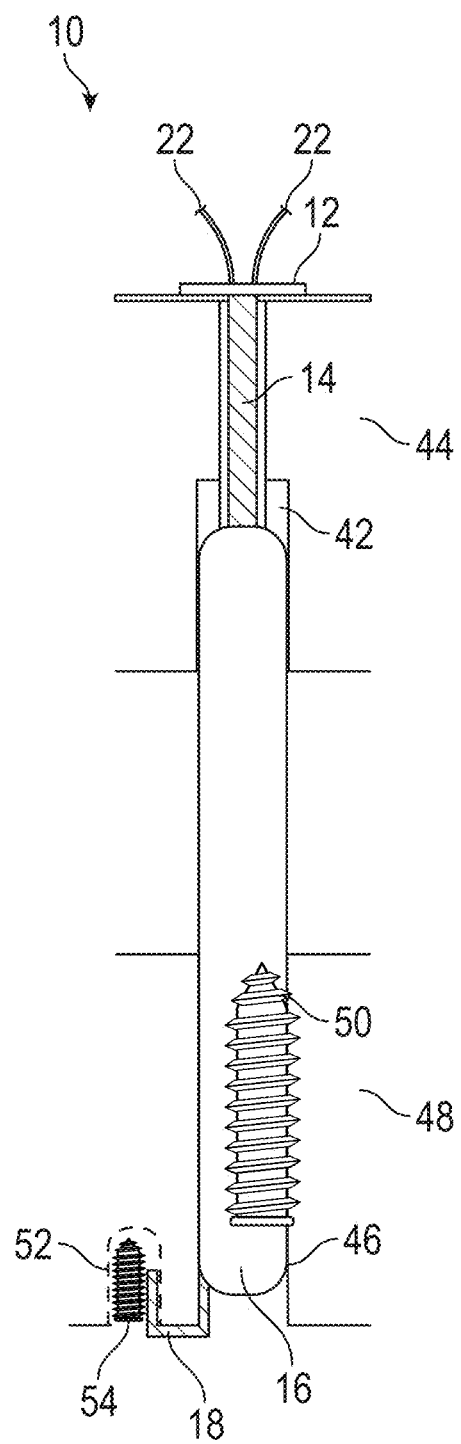
FIG. 10 illustrates an exemplary fixation of a reinforcement material and a graft as part of the tissue reconstruction procedure of FIG. 9.

Fixation of the graft 16 and the reinforcement material 18 to the second bone 48 can be achieved in a variety of ways. In a first embodiment, shown in FIG. 10, the graft 16 may be fixated within the second bone tunnel 46 using a first interference screw 50 (or first suture anchor) and the reinforcement material 18 may be fixated within a bone hole 52 of the second bone 48 using a second interference screw 54 (or second suture anchor). The bone hole 52 is a separate opening of the second bone 48 from the second bone tunnel 46.

Figure 11:
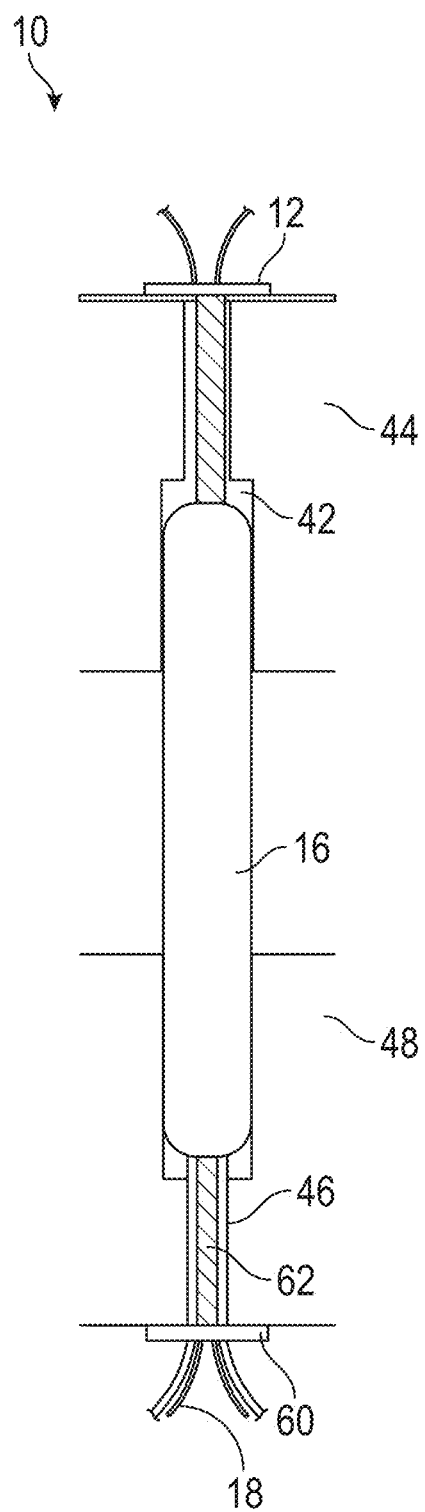
FIG. 11 illustrates another exemplary fixation of the reinforcement material and the graft as part of the tissue reconstruction procedure of FIG. 9.

Alternatively, as shown in FIG. 11, the graft 16 and the reinforcement material 18 may be fixated relative to the second bone 48 using a second fixation device 60 (e.g., a second button) and a second adjustable loop 62 that is carried by the second fixation device 60.

Figure 12:
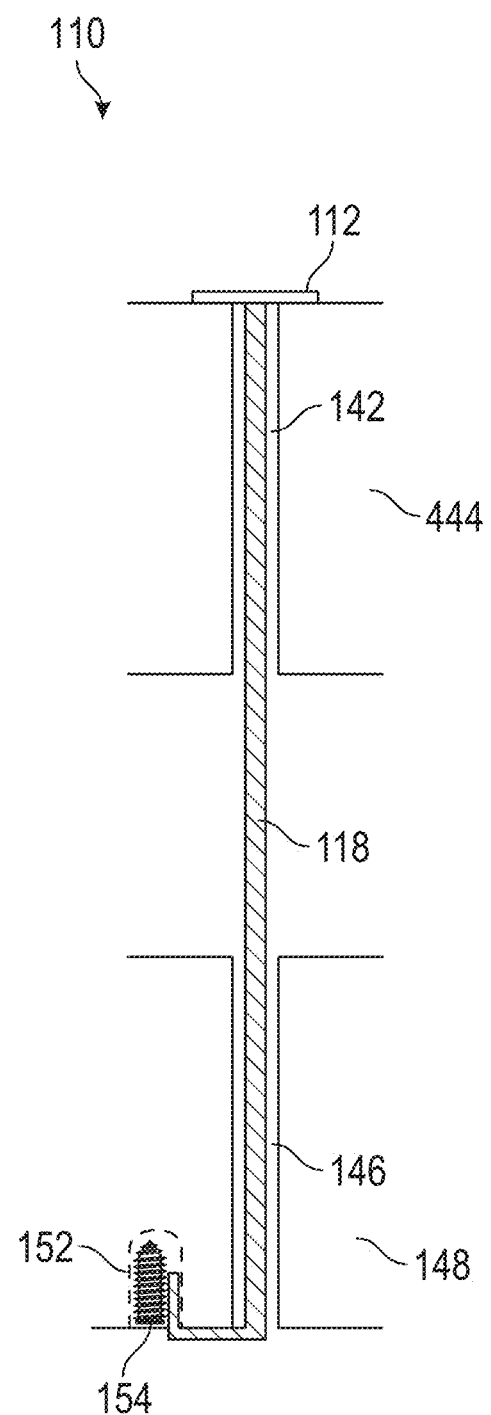
FIG. 12 schematically illustrates a use of a surgical fixation system as part of a tissue repair procedure.

FIG. 12 illustrates an exemplary surgical use of a surgical fixation system 110 during a tissue repair procedure, such as an ACL repair procedure. The surgical fixation system 110 can be used in situations where a native ligament (e.g., an ACL) needs repaired but does not require a complete reconstruction. It should be understood that this disclosure is not limited to ACL repair procedures, and the surgical fixation system 110 could be used in a variety of repair procedures within the scope of this disclosure.

The exemplary surgical fixation system 110 includes a fixation device 112, such as a button, and a reinforcement material 118, such as suture tape. The reinforcement material 118 is connected to the fixation device 112. For example, the reinforcement material 118 could be looped through openings of the fixation device 112. Unlike the surgical fixation system 10 of FIG. 1, the surgical fixation system 110 of FIG. 12 excludes a loop or graft since the native ligament is only being repaired as opposed to being completely reconstructed using a graft.

In an exemplary embodiment, the surgical fixation system 110 is implanted by passing the fixation device 112 through a first bone tunnel 142 of a first bone 144 and a second bone tunnel 146 of a second bone 148. The fixation device 112 may be pulled through the first and second bone tunnels 142, 146 using a passing suture (not shown) and self-flips onto the cortex of the first bone 144 once tension is released on the passing suture.

After passing and flipping the fixation device 112, the fixation device 112 suspends the reinforcement material 118 within portions of the first bone tunnel 142 and the second bone tunnel 146. The reinforcement material 118 may extend out of the second bone tunnel 146 and can be tensioned separately from the native ligament prior to completing the repair. Because the native ligament and the reinforcement material 118 may be tensioned separately from one another, a different amount of tension is left in the reinforcement material 118 compared to the native ligament. This creates a load sharing environment between the native ligament and the reinforcement material 118 in which the reinforcement material 118 is configured to augment the strain threshold of the native ligament.

Fixation of the reinforcement material 118 to the second bone 148 can be achieved in a variety of ways. In an embodiment, the reinforcement material 118 may be fixated within a bone hole 152 of the second bone 148 using a screw 154 (or suture anchor). The bone hole 152 is a separate opening of the second bone 148 from the second bone tunnel 146.

EXAMPLES

Figure 13:
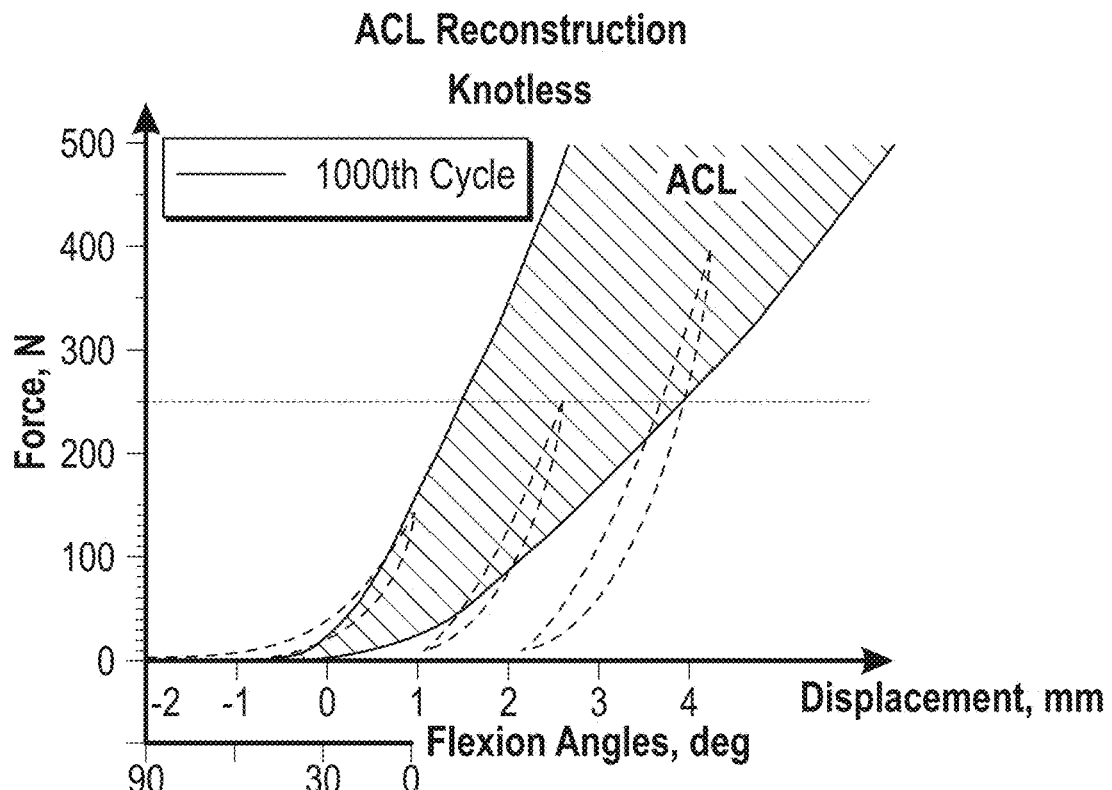
FIG. 13 is a graph illustrating force versus displacement during testing of a sample surgical fixation system that has been used in a tissue reconstruction procedure.

Example 1: Displacement Testing of a Surgical Fixation System Used in an ACL Reconstruction Procedure A surgical fixation system similar to the system 10 of FIG. 1 was used to perform an ACL reconstruction procedure. The surgical fixation system was then tested by measuring force (in newtons) versus displacement (in mm). The results of this testing are shown in the plot of FIG. 13.

Figure 14:
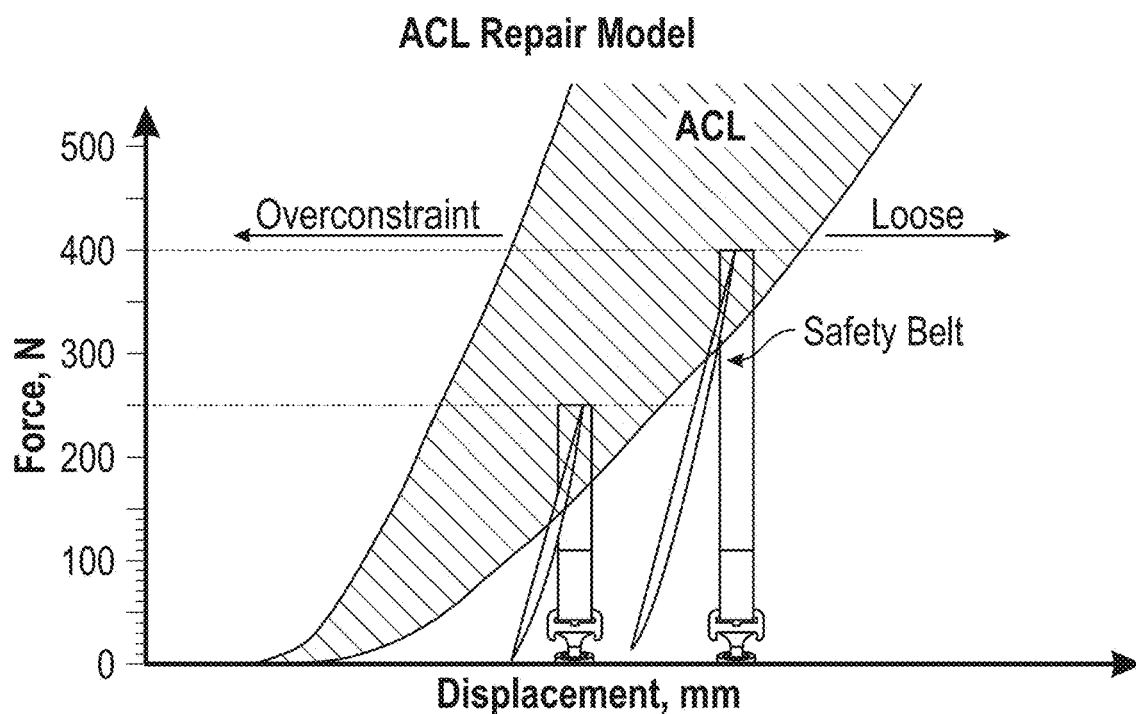
FIG. 14 is a graph illustrating force versus displacement during testing of a sample surgical fixation system that has been used in a tissue repair procedure.

Example 2: Displacement Testing of a Surgical Fixation System Used in an ACL Repair Procedure A surgical fixation system similar to the system 110 shown in FIG. 12 was used to perform an ACL repair procedure. The surgical fixation system was then tested by measuring force (in newtons) versus displacement (in mm). The results of this testing are shown in the plot of FIG. 14.

Example 3: Elongation Testing of a Surgical Fixation System

Figure 15:
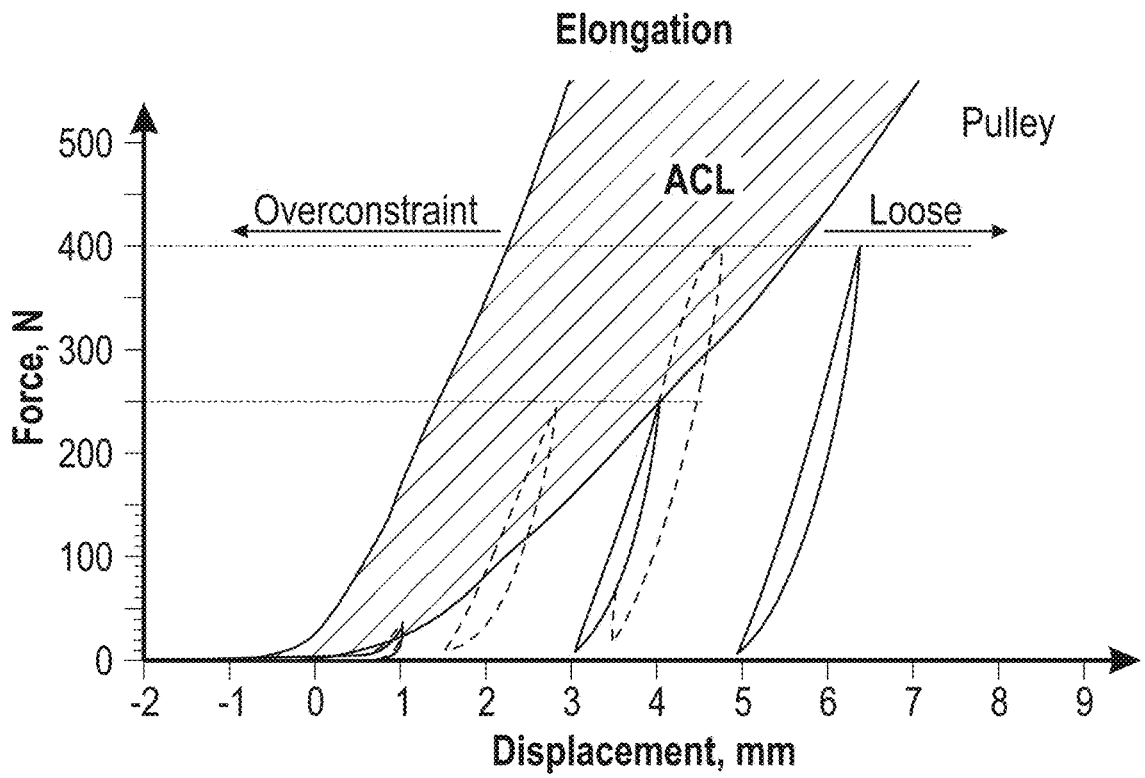
FIG. 15 is a graph illustrating elongation behavior of a sample surgical fixation system.

A surgical fixation system similar to the system 10 of FIG. 1 was used to perform an ACL reconstruction procedure. The surgical fixation system was then tested by measuring force (in newtons) versus displacement (in mm) using a pulley testing technique. The results of this testing are shown in the plot of FIG. 15.

Example 4: Elongation Testing of Another Surgical Fixation System

Figure 16:
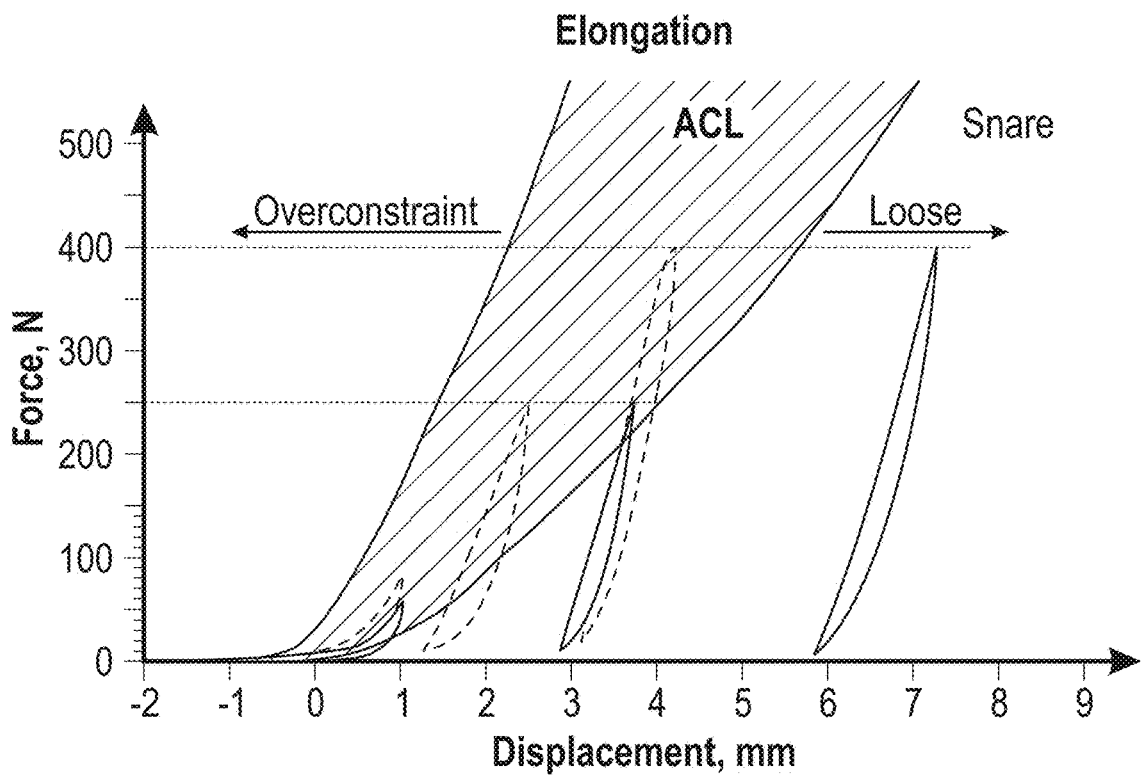
FIG. 16 is another graph illustrating elongation behavior of a sample surgical fixation system.

A surgical fixation system similar to the system 10 of FIG. 1 was used to perform an ACL reconstruction procedure. The surgical fixation system was then tested by measuring force (in newtons) versus displacement (in mm) using a snare testing technique. The results of this testing are shown in the plot of FIG. 16.

Example 5: Pull Out Testing

Figure 17:
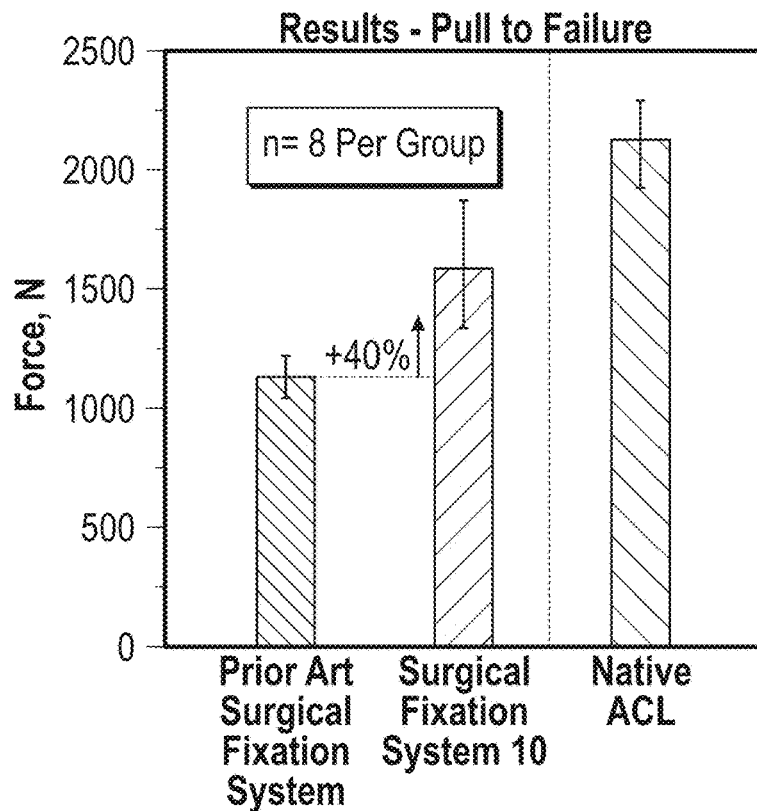
FIG. 17 is a bar graph illustrating pull out forces of a sample surgical fixation system as compared to a prior art surgical fixation system and a native anterior cruciate ligament.

A surgical fixation system similar to the system 10 of FIG. 1 was used to perform an ACL reconstruction procedure. The surgical fixation system was tested against both a prior art surgical fixation system and a native ACL by measuring pull to failure forces (in newtons). The results of this testing are shown in the bar graph of FIG. 17. The surgical fixation system exhibited a 40% increase in pull out strength compared to the prior art surgical fixation system.

Example 6: Stiffness Testing

Figure 18:
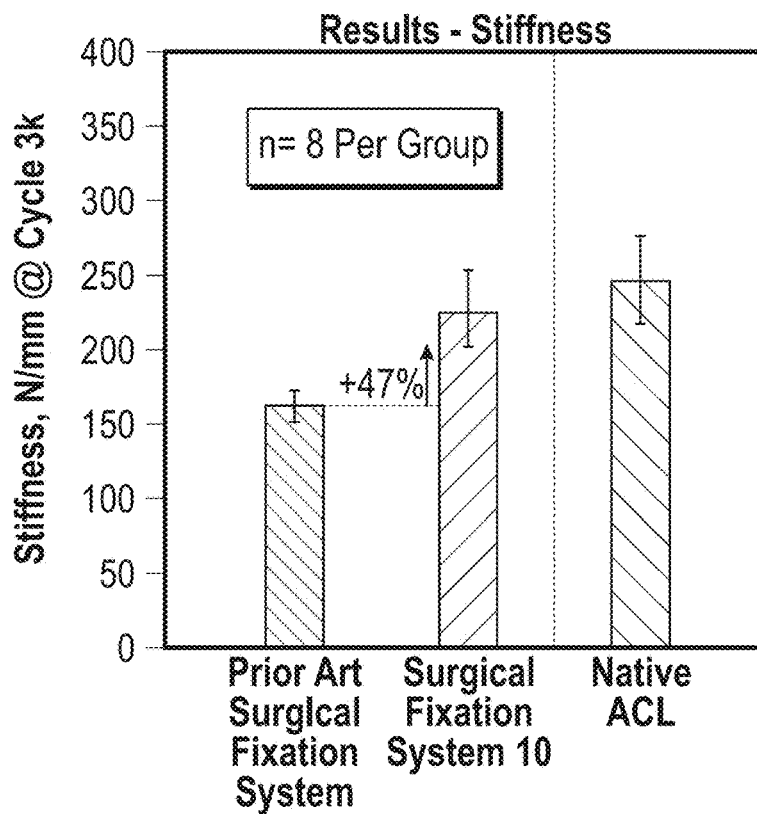
FIG. 18 is a bar graph illustrating stiffness results of a sample surgical fixation system as compared to a prior art surgical fixation system and a native anterior cruciate ligament.

A surgical fixation system similar to the system 10 of FIG. 1 was used to perform an ACL reconstruction procedure. The surgical fixation system was then tested against both a prior art surgical fixation system and a native ACL by measuring the relative stiffness (in N/mm) of each construct. The results of this testing are shown in the bar graph of FIG. 18. The surgical fixation system exhibited a 47% increase in stiffness compared to the prior art surgical fixation system.

Example 7: Dynamic Elongation Testing

Figure 19:
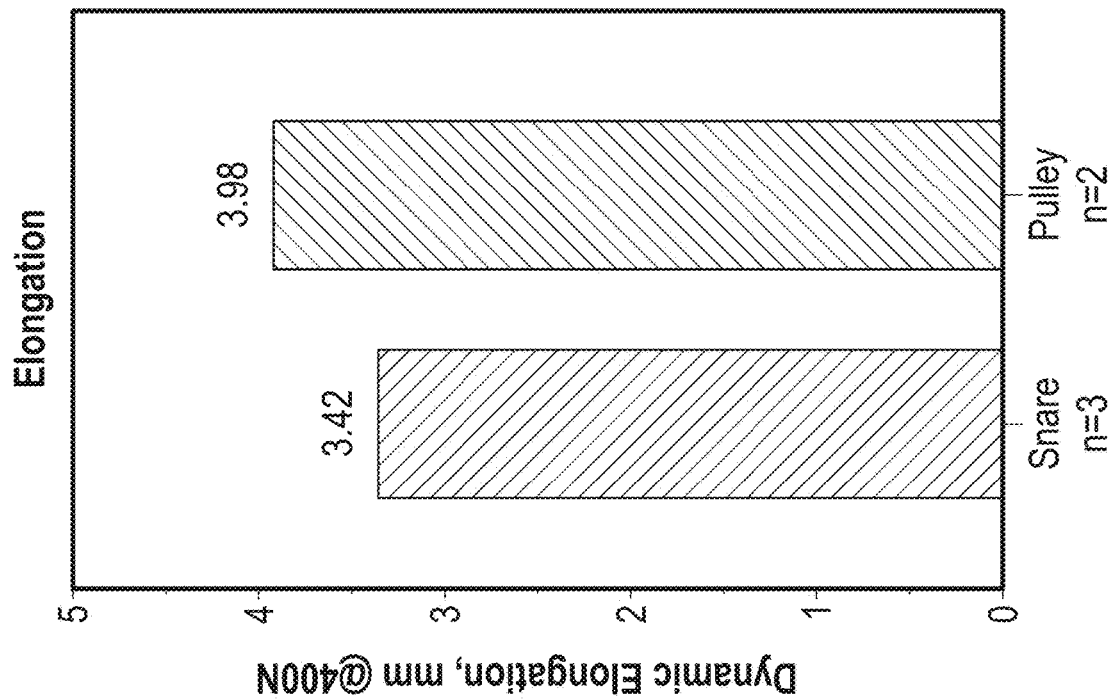
FIG. 19 is a bar graph illustrating elongation behavior of a sample surgical fixation system.
Figure 19:
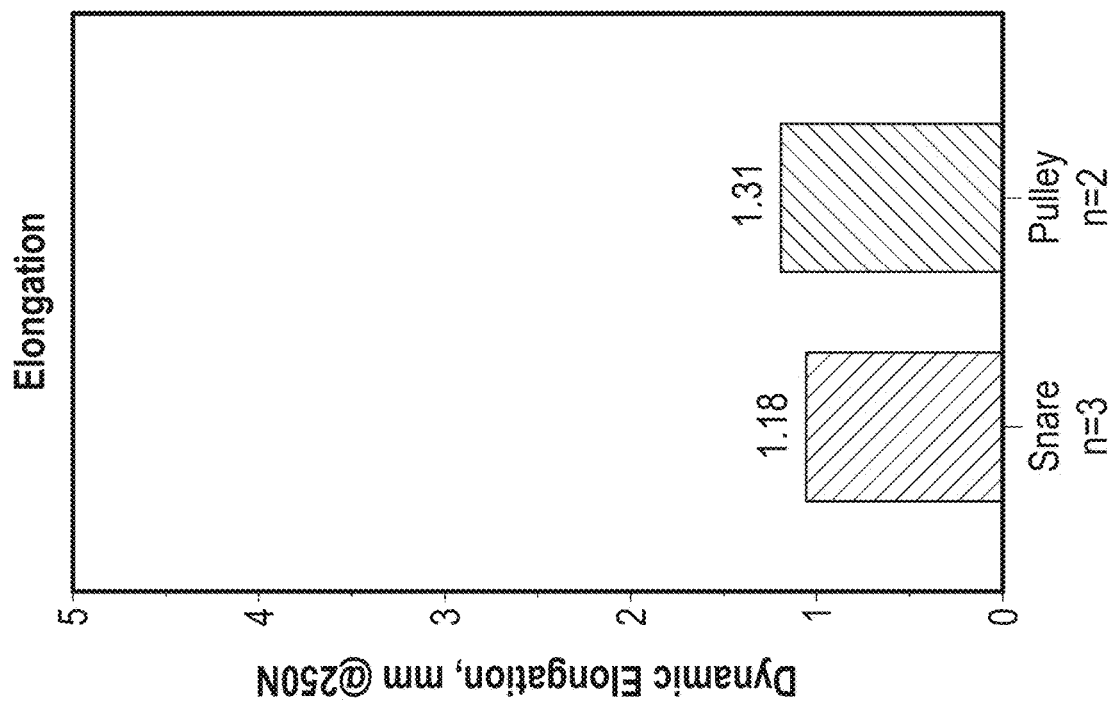

A surgical fixation system similar to the system 10 of FIG. 1 was used to perform an ACL reconstruction procedure. The surgical fixation system was then tested by measuring dynamic elongation at forces of 250 N and 400 N using both a snare testing technique and a pulley testing technique. The results of this testing are shown in the bar graphs of FIG. 19.

Example 8: Pull to Fail and Stiffness Testing

Figure 20:
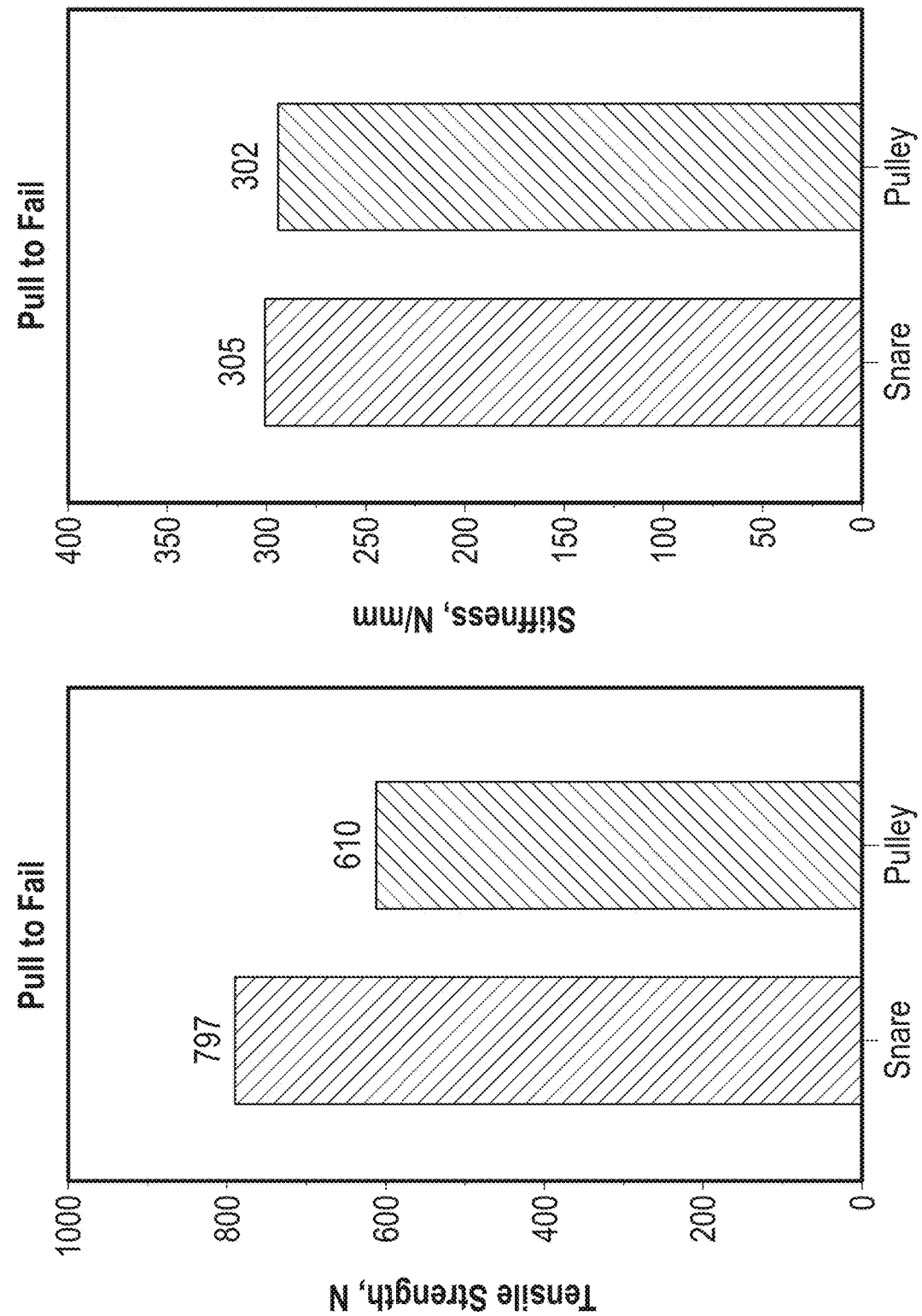
FIG. 20 is a bar graph illustrating pull to failure and stiffness testing results of a sample surgical fixation system.

A surgical fixation system similar to the system 10 of FIG. 1 was used to perform an ACL reconstruction procedure. The surgical fixation system was then tested by measuring tensile strength (in newtons) and stiffness (in N/mm) using both a snare testing technique and a pulley testing technique. The results of this testing are shown in the bar graphs of FIG. 20.

Figure 21:
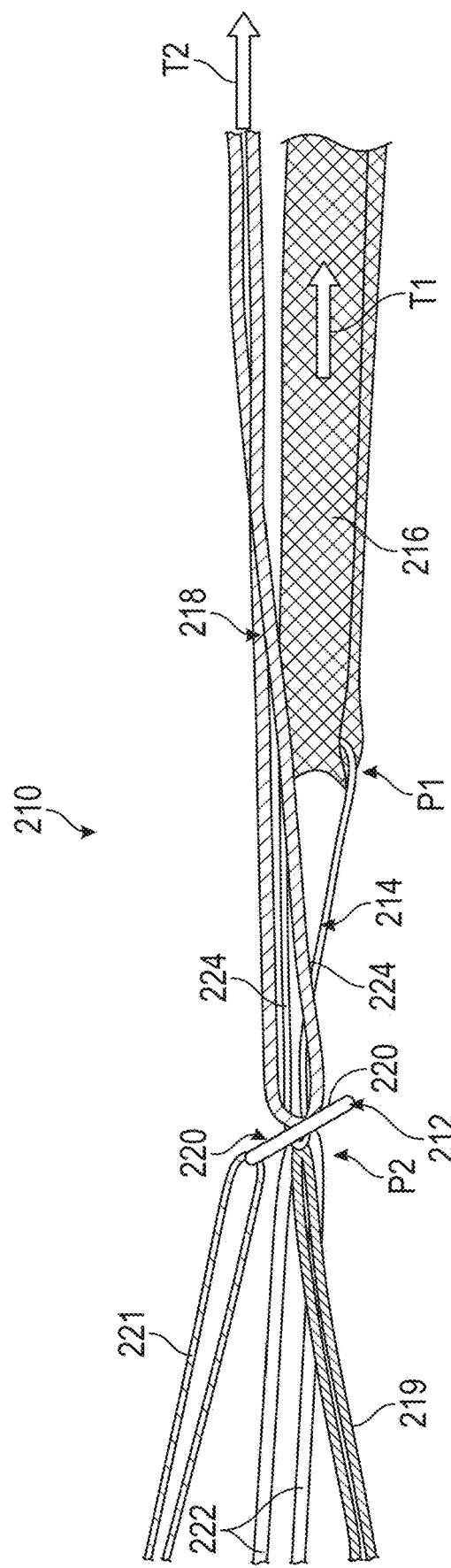
FIG. 21 illustrates another exemplary surgical fixation system for performing a tissue reconstruction procedure.

FIG. 21 illustrates another exemplary surgical fixation system 210. The surgical fixation system 210 includes a fixation device 212, a loop 214, a graft 216, a reinforcement material 218, a passing strand 219, and a flipping strand 221. The fixation device 212 provides cortical bone fixation of the graft 216 after the graft 216 has been positioned within a bone tunnel. In another embodiment, the fixation device 212 includes one or more apertures 220 formed through the body of the fixation device 212 for receiving the loop 214, the reinforcement material 218, and the passing strand 219.

The loop 214 may be an adjustable loop made of a flexible material and includes an adjustable length and perimeter. Free braid strands 222 of the loop 214 may be pulled to reduce the size of the loop 214. For example, the loop 214 may be adjusted in a first direction by pulling the free braid stands 222 but is prevented from loosening in the opposite direction due to applied internal tensile forces.

The loop 214 may include one or more adjustable eye-splices 224 that are formed by splicing the flexible material that is used to form the loop 214 through itself. The loop 214 is connected to the fixation device 212 prior to completely forming the loop 214.

The graft 216 is connected at a first fixation location P1 of the surgical fixation system 210. In an exemplary embodiment, the graft 216 is connected to the loop 214, and thus, the first fixation location P1 is at a cradle of the loop 214. For example, the graft 216 may be looped over a portion of the loop 214.

The reinforcement material 218 may be a suture construct. The reinforcement material 218 is connected at a second fixation location P2 of the surgical fixation system 210. The second fixation location P2 is a different location from the first fixation location P1. In an exemplary embodiment, the second fixation location P2 is at the fixation device 212. The size of the fixation device 12 can be adjusted to accommodate the addition of the reinforcement material 218. The reinforcement material 218 may be passed through the apertures 220 of the fixation device 212 to connect the reinforcement material 218 to the surgical fixation system 210. The reinforcement material 18 is thus unconnected in any way to the graft 216. The reinforcement material 218 may be used to augment a ligament repair procedure and acts as a reinforcement that supports the primary repair provided by the graft 216. The reinforcement material 218 may therefore be referred to as a "safety belt."

In another exemplary embodiment, the graft 216 and the reinforcement material 218 can be tensioned separately from one another, resulting in independent tension loads. This is possible because these components are connected at the separate fixation locations P1, P2, respectively, of the surgical fixation system 210. For example, a first tension T1 may be applied to the graft 216, whereas a second, different tension T2 may be applied to the reinforcement material 218 during implantation of the surgical fixation system 210. Tension can also be reapplied to the graft 216 after tensioning the reinforcement material 218. Accordingly, joint loads may be shared between the graft 216 and the reinforcement material 218, with the reinforcement material 218 acting as a dynamic joint stabilizer that shares loads with the graft 216 according to its relative initial tensioning.

Figure 22:
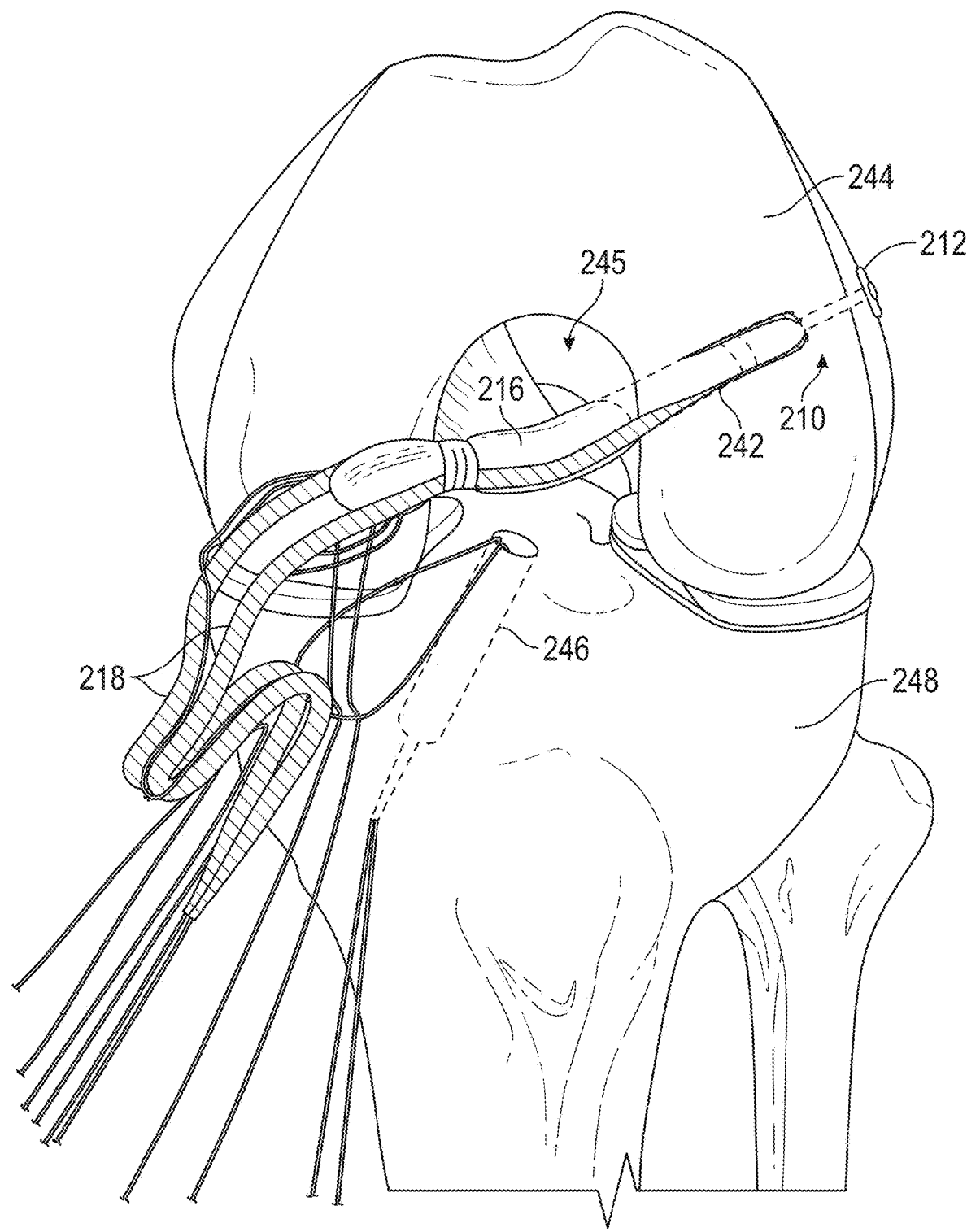
FIGS. 22, 23, and 24 schematically illustrate a use of the surgical fixation system of FIG. 21 as part of a tissue reconstruction procedure.
Figure 23:
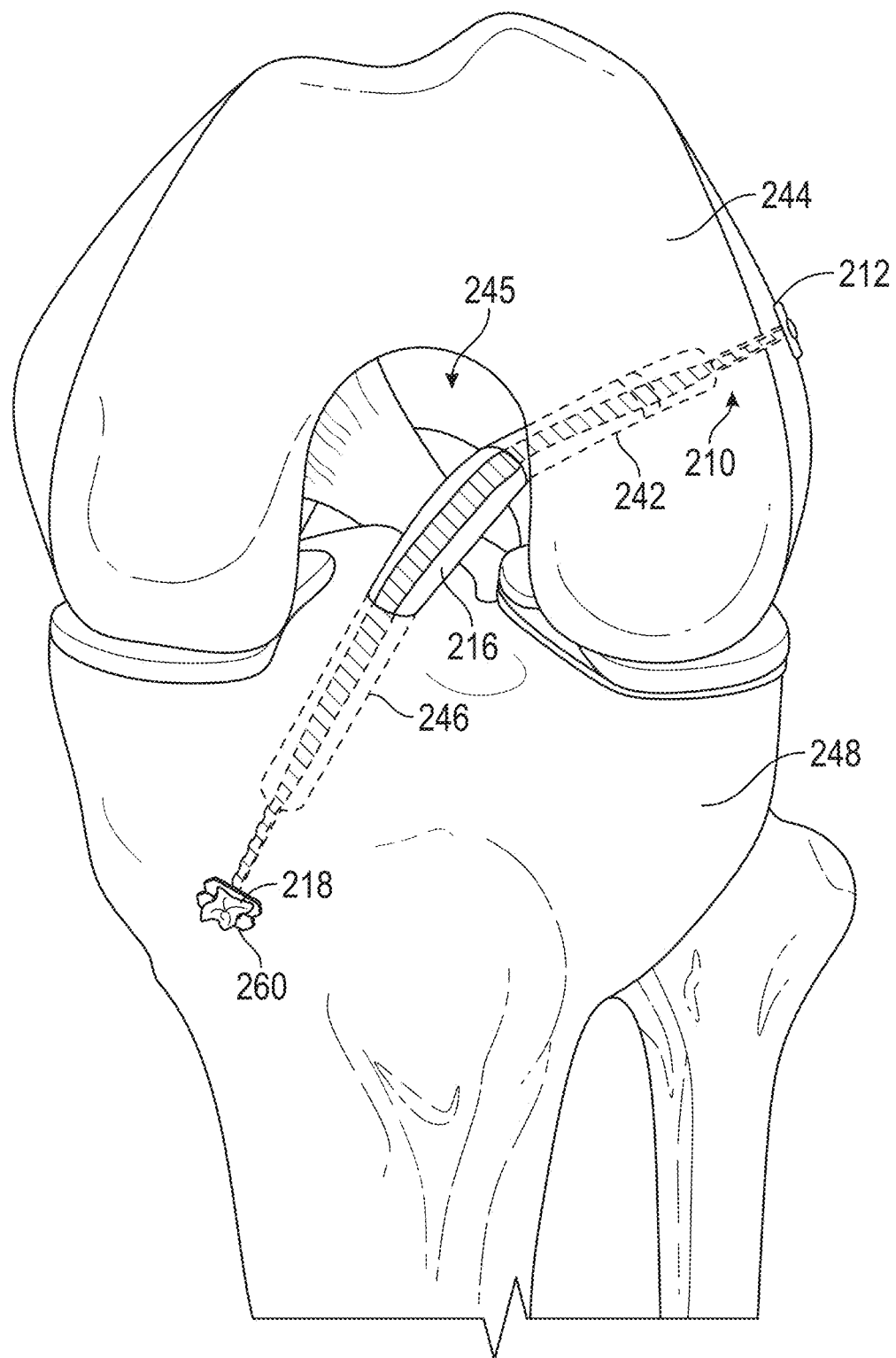
Figure 24:
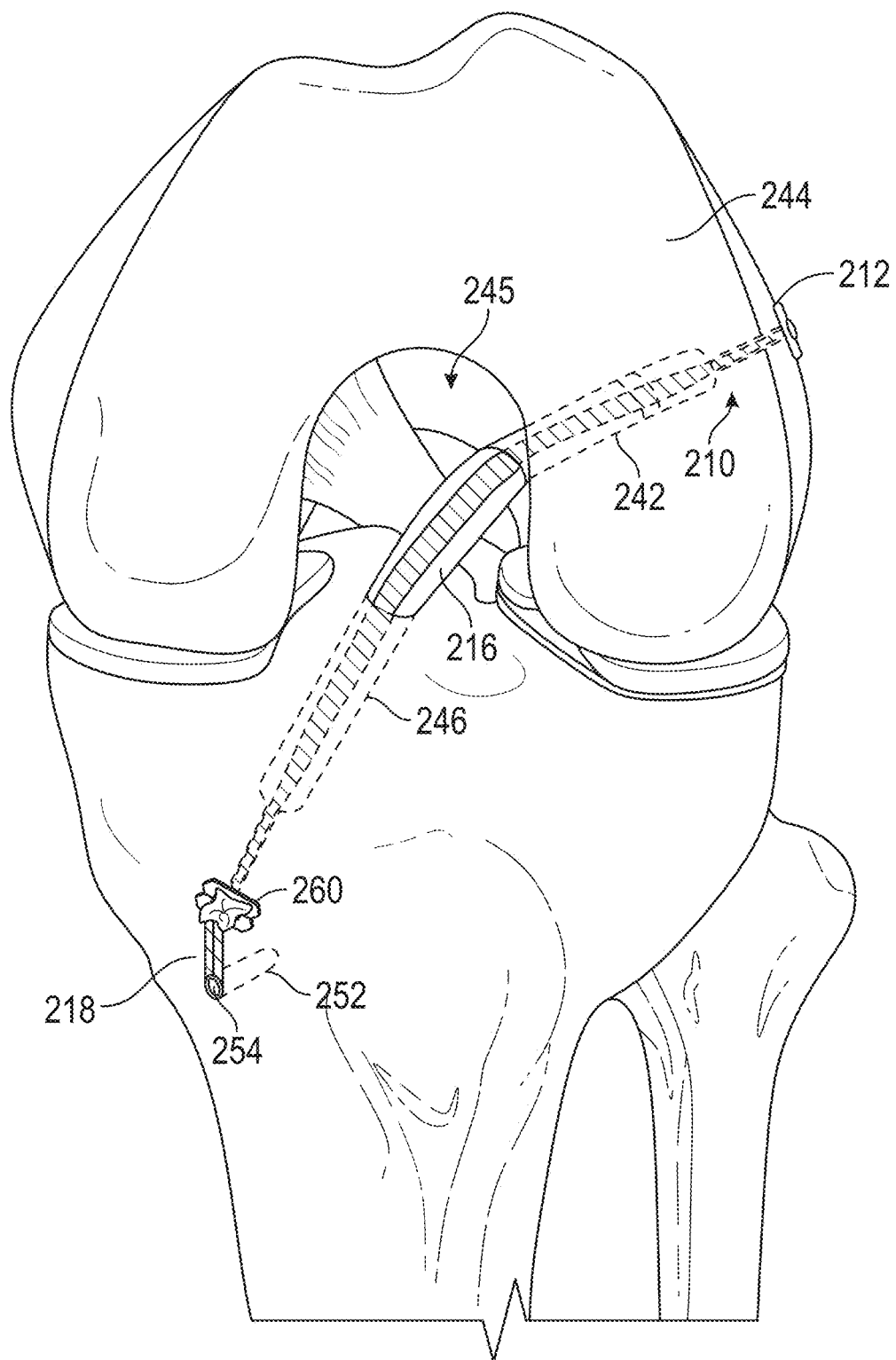

FIGS. 22-24 schematically illustrate an exemplary surgical use of the surgical fixation system 210 of FIG. 21 during a tissue reconstruction procedure, such as an ACL reconstruction procedure. The surgical fixation system 210 may be implanted within a joint 245 (e.g., a knee joint) to repair a torn tissue (e.g., a torn ACL). Prior to positioning the surgical fixation system 210 within the joint 245, a first bone tunnel 242 (e.g., a socket) is formed in a first bone 244 (e.g., a femur) and a second bone tunnel 246 (e.g., a passage) is formed in a second bone 248 (e.g., a tibia).

In an exemplary embodiment, fixation of the surgical fixation system 10 includes inserting the graft 216 relative to the first bone 244 by passing the fixation device 212 through the first bone 244, inserting the graft 216 relative to the second bone 248, precycling the construct over a full flexion range, re-tensioning a tibial side of the graft 216 in full extension, and then re-tensioning the femoral side of the graft 216 in full extension.

Fixation of the graft 216 and the reinforcement material 218 to the second bone 248 can be achieved in a variety of ways. In a first embodiment, shown in FIG. 23, both the graft 216 and the reinforcement material 218 may be fixated within the second bone tunnel 46 using a second fixation device 260 (e.g., a second button). Alternatively, as shown in FIG. 24, the graft 216 may be fixated using a second fixation device 260 while the reinforcement material 218 is fixated in a separate bone hole 252 using a screw 254.

Additional Examples

Figure 25:
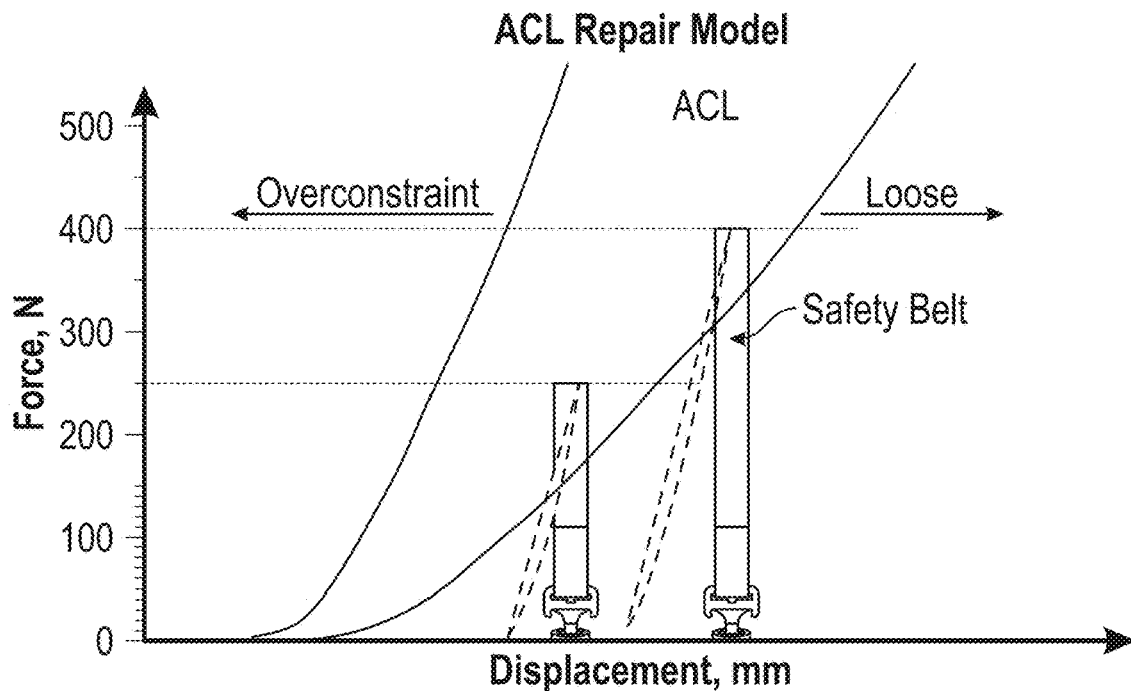
FIG. 25 is a graph illustrating force versus displacement during testing of a sample surgical fixation system that has been used in a tissue repair procedure.

Example 9: Displacement Testing of a Surgical Fixation System Used in an ACL Repair Procedure A surgical fixation system similar to the system 210 shown in FIG. 21 was used to perform an ACL repair procedure. The surgical fixation system was then tested by measuring force (in newtons) versus displacement (in mm). The results of this testing are shown in the plot of FIG. 25.

Figure 26:
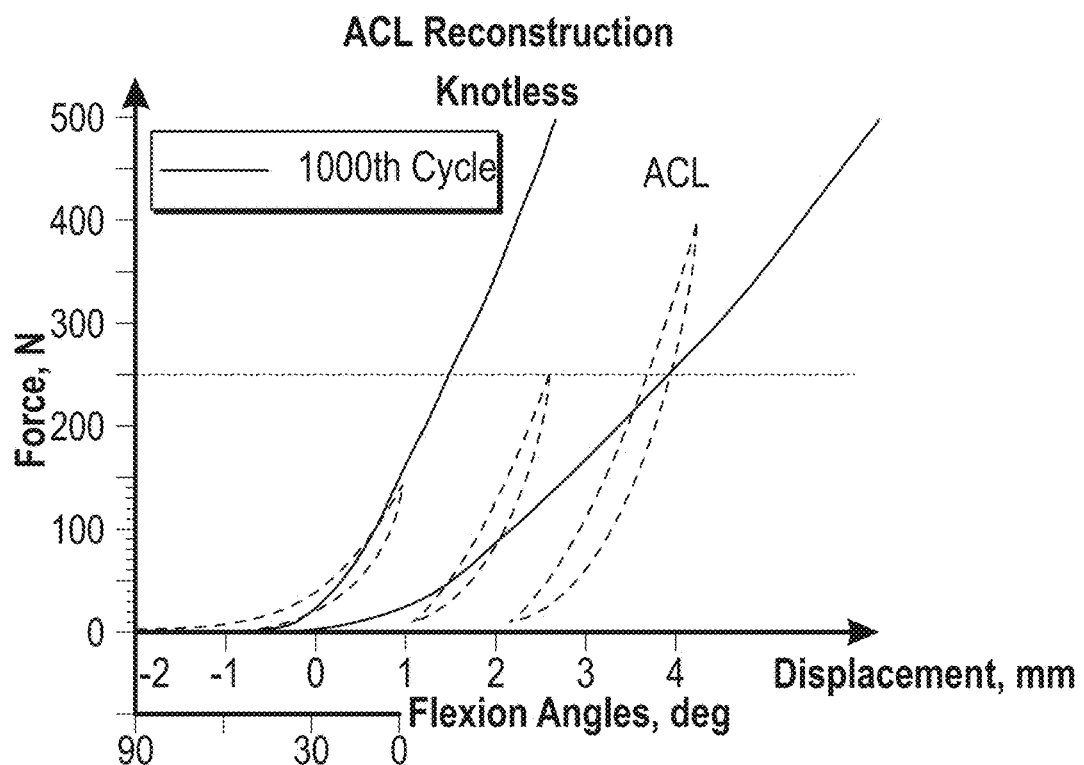
FIG. 26 is a graph illustrating force versus displacement during testing of a sample surgical fixation system that has been used in a tissue reconstruction procedure.

Example 10: Displacement Testing of a Surgical Fixation System Used in an ACL Reconstruction Procedure A surgical fixation system similar to the system 210 shown in FIG. 21 was used to perform an ACL reconstruction procedure. The surgical fixation system was then tested by measuring force (in newtons) versus displacement (in mm). The results of this testing are shown in the plot of FIG. 26.

Example 11: Stiffness Testing

Figure 27:
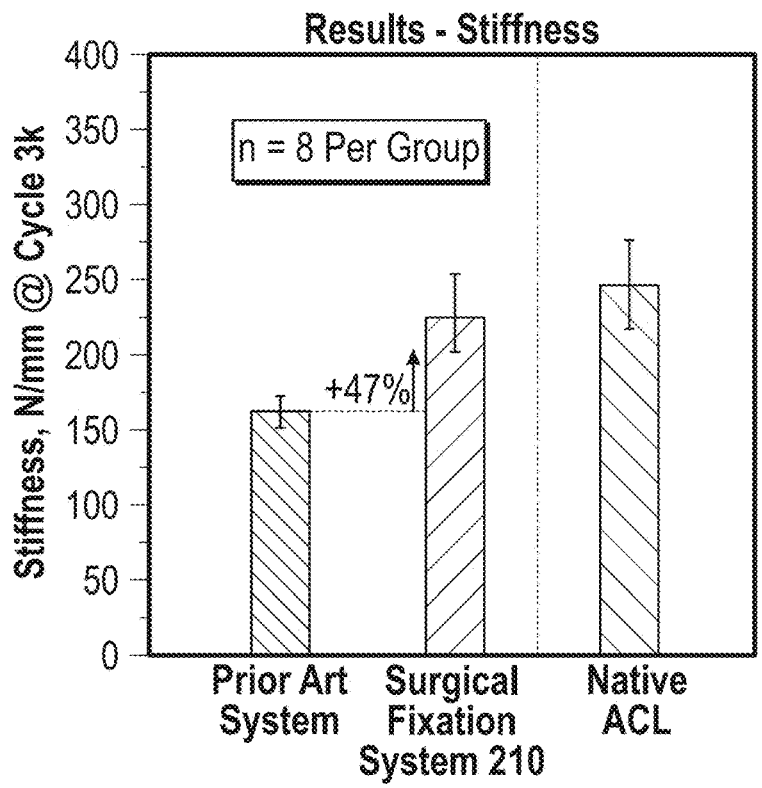
FIG. 27 is a bar graph illustrating stiffness results of a sample surgical fixation system as compared to a prior art surgical fixation system and a native anterior cruciate ligament.

A surgical fixation system similar to the system 210 of FIG. 21 was used to perform an ACL reconstruction procedure. The surgical fixation system was then tested against both a prior art surgical fixation system and a native ACL by measuring the relative stiffness (in N/mm) of each construct. The results of this testing are shown in the bar graph of FIG. 27. The surgical fixation system exhibited a 47% increase in stiffness compared to the prior art surgical fixation system.

Example 12: Pull to Failure Testing

Figure 28:
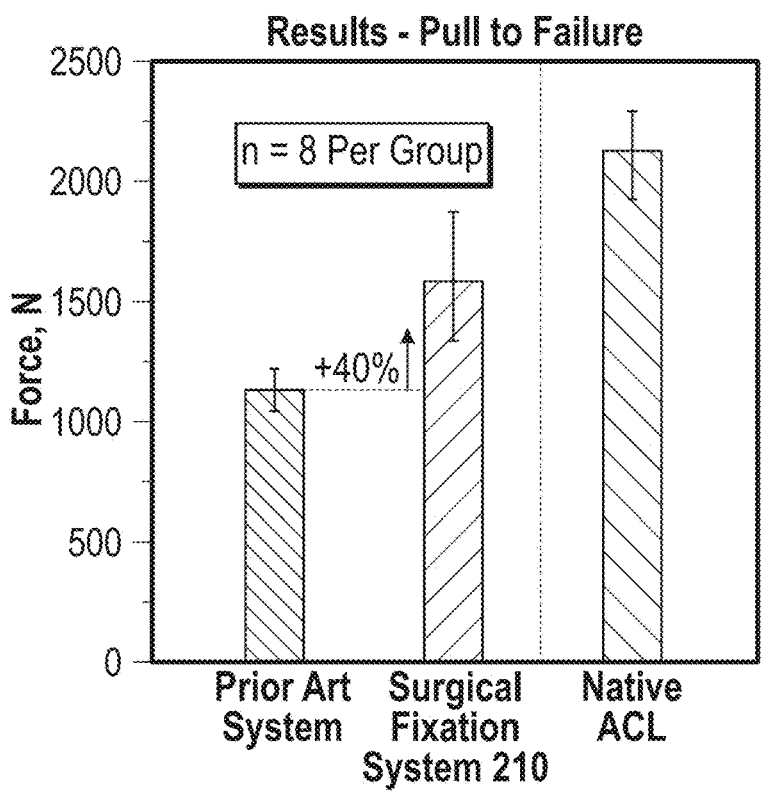
FIG. 28 is a bar graph illustrating pull to failure forces of a sample surgical fixation system as compared to a prior art surgical fixation system and a native anterior cruciate ligament.

A surgical fixation system similar to the system 210 of FIG. 21 was used to perform an ACL reconstruction procedure. The surgical fixation system was tested against both a prior art surgical fixation system and a native ACL by measuring pull to failure forces (in newtons). The results of this testing are shown in the bar graph of FIG. 28. The surgical fixation system exhibited a 40% increase in pull out strength compared to the prior art surgical fixation system.

Example 13: Bovine Tendon Graft Model

Figure 29:
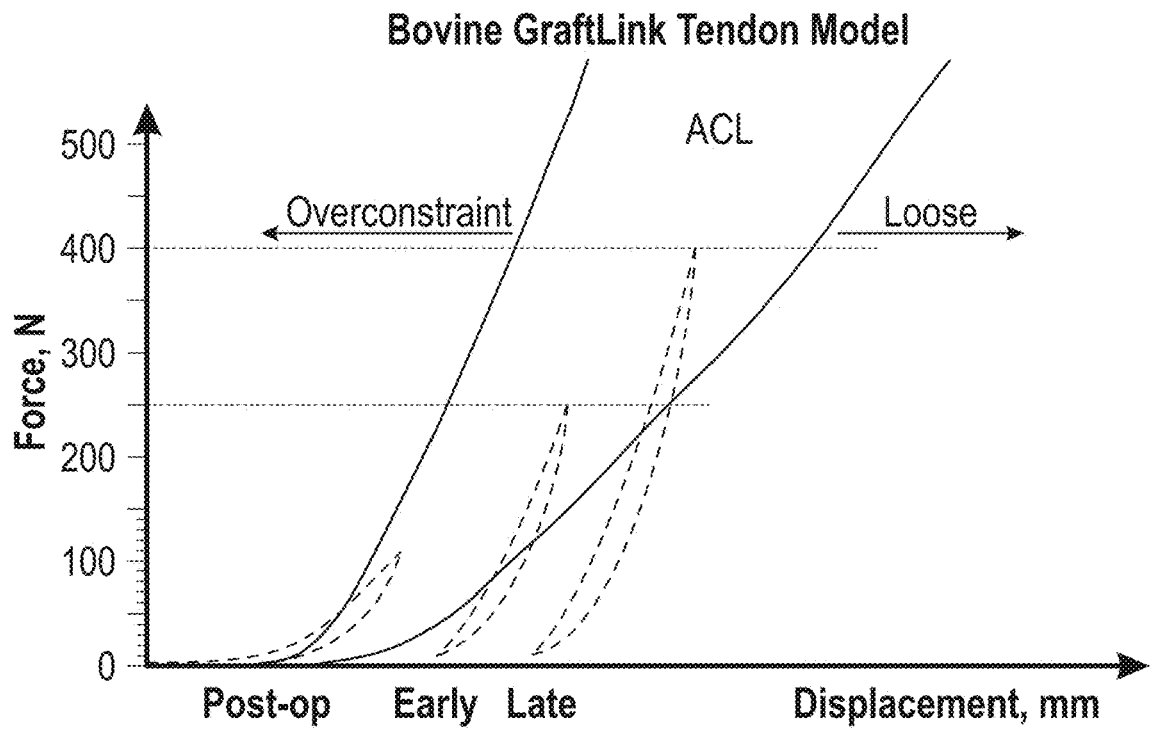
FIGS. 29, 30, 31, 32, and 33 schematically illustrate testing of a surgical fixation system in a bovine model.
Figure 30:
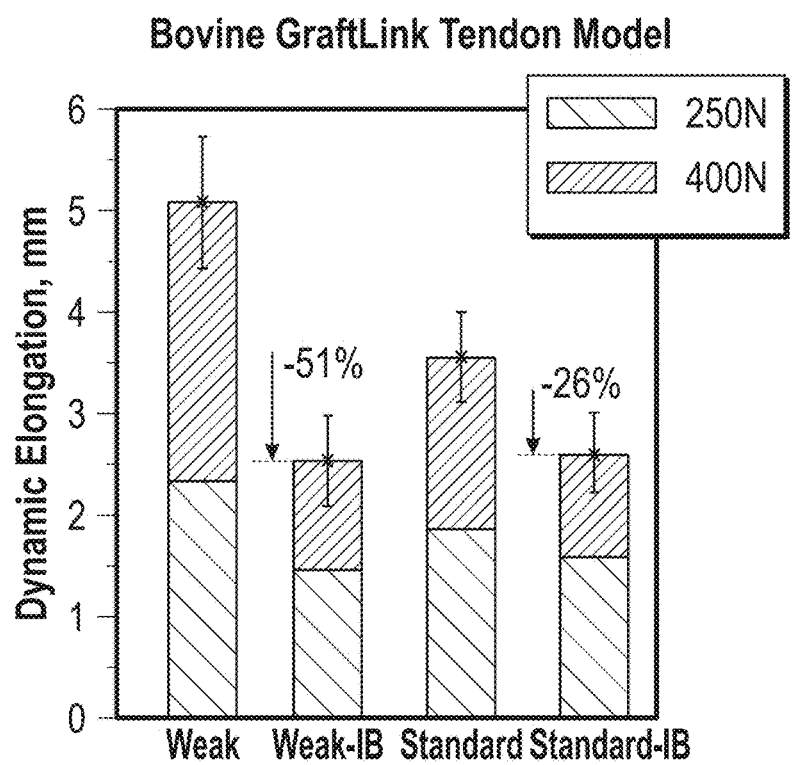
Figure 31:
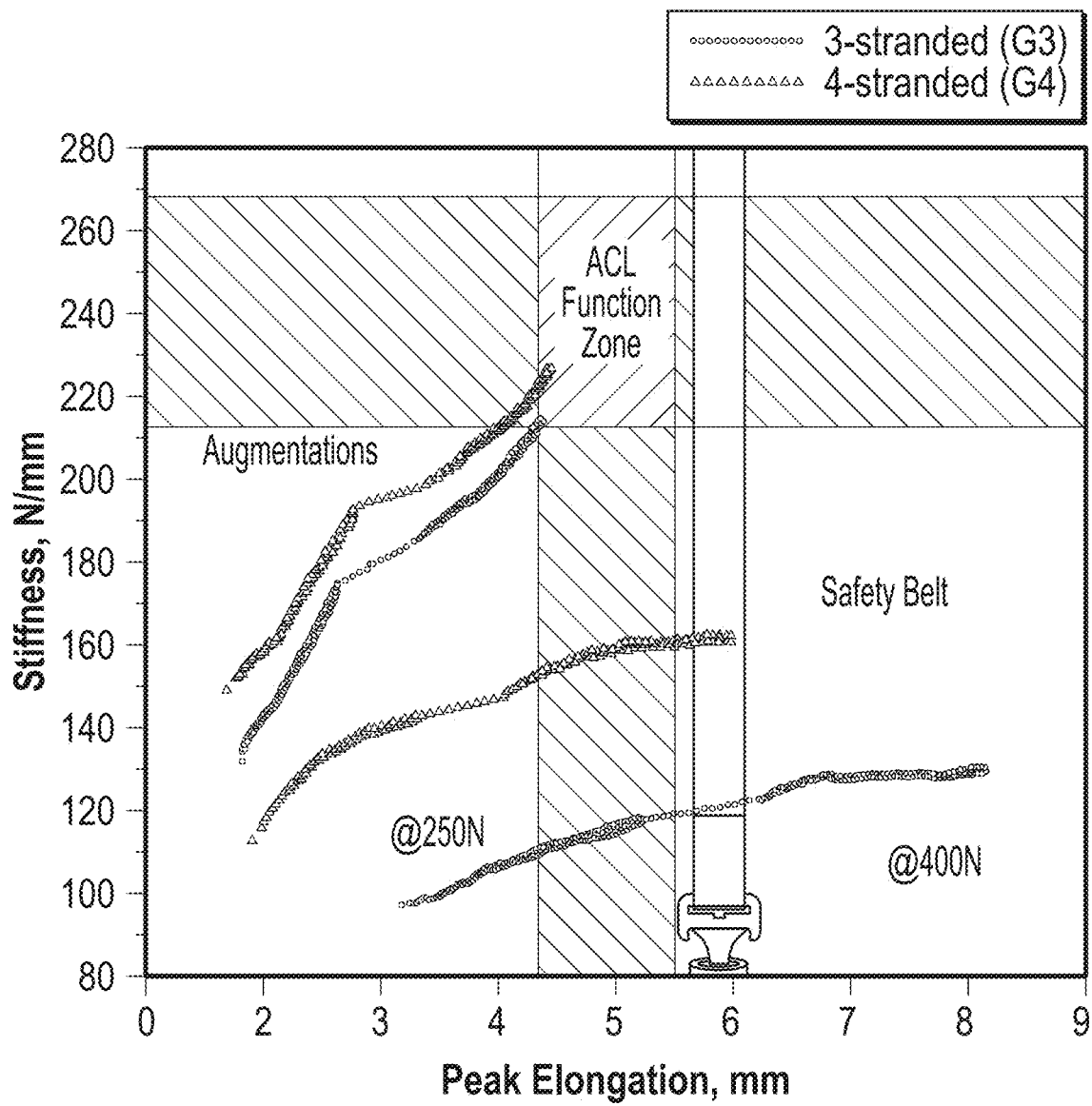
Figure 32:
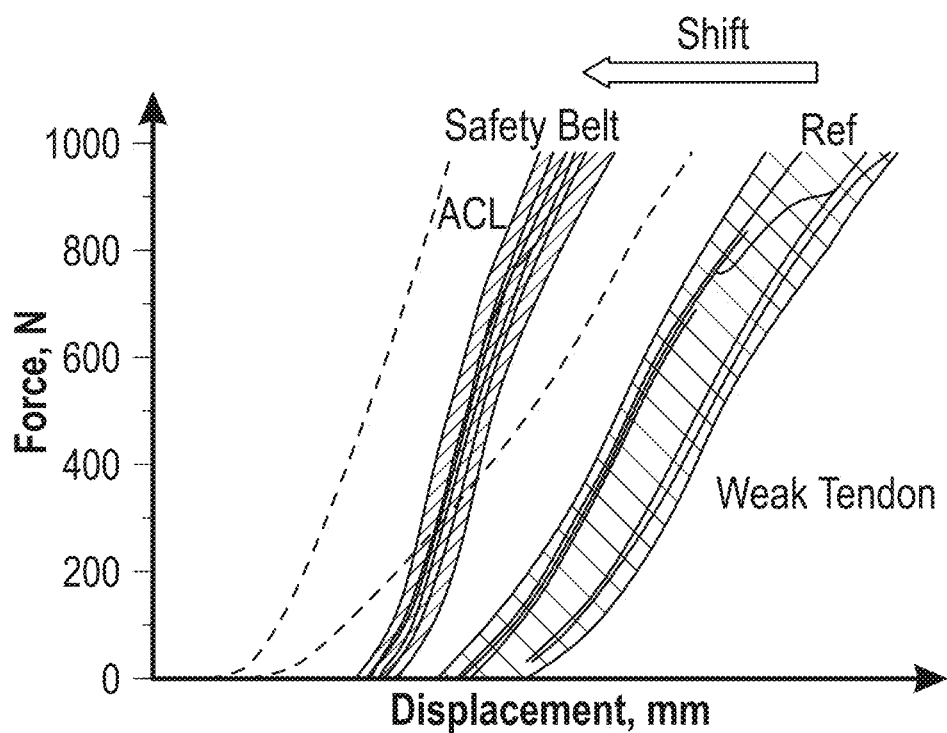
Figure 32:
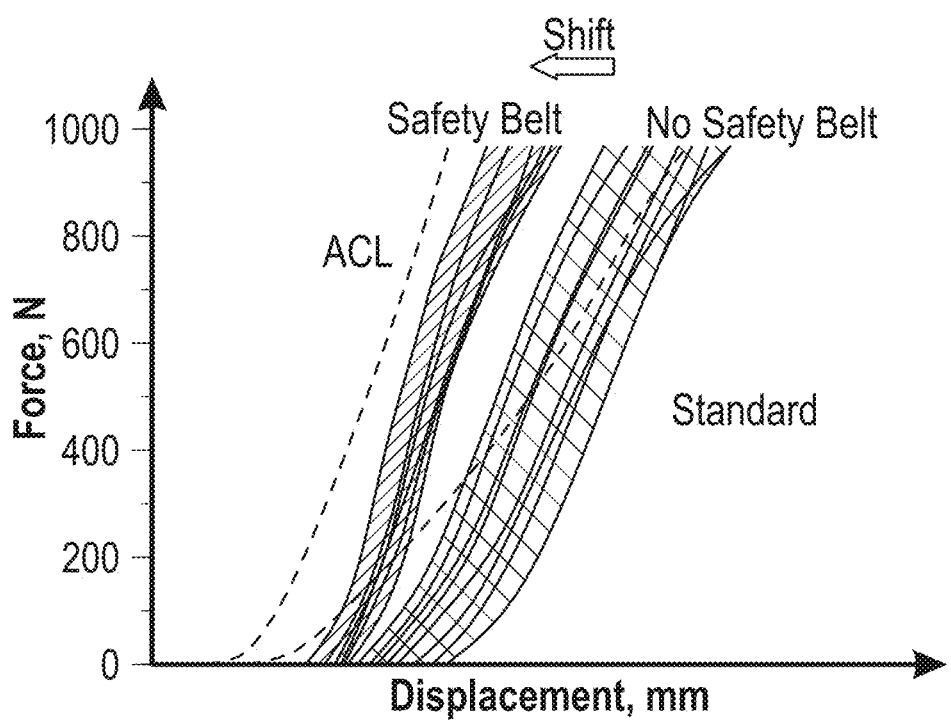
Figure 33:
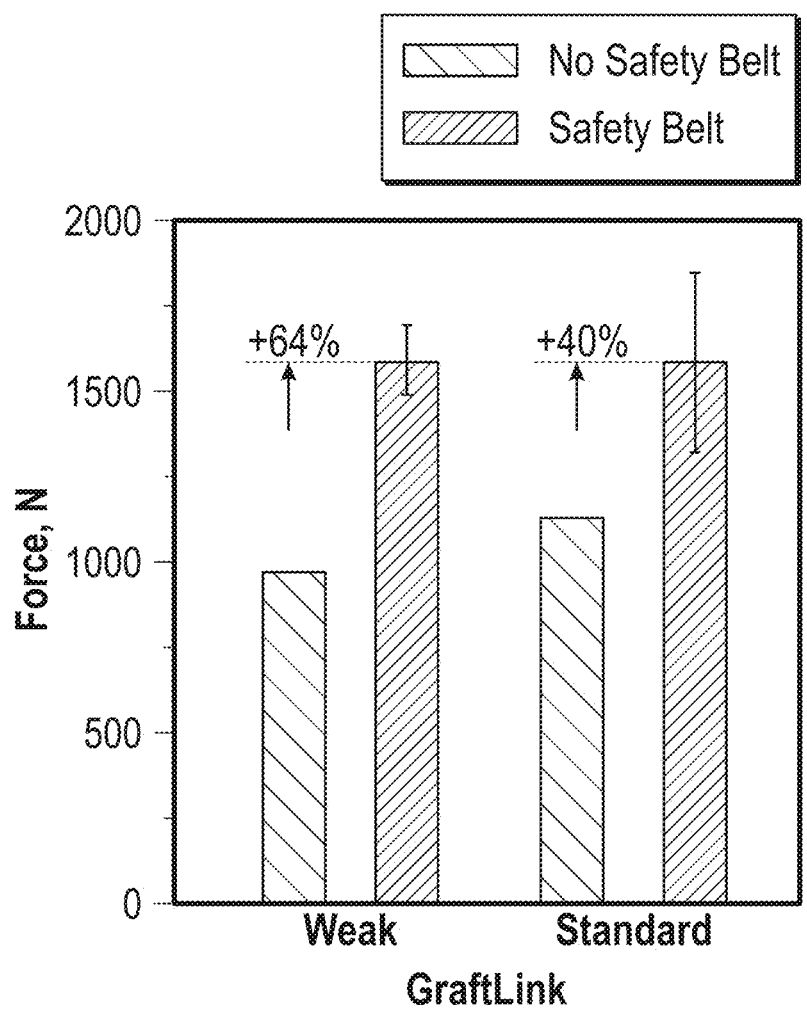
Figure 34:
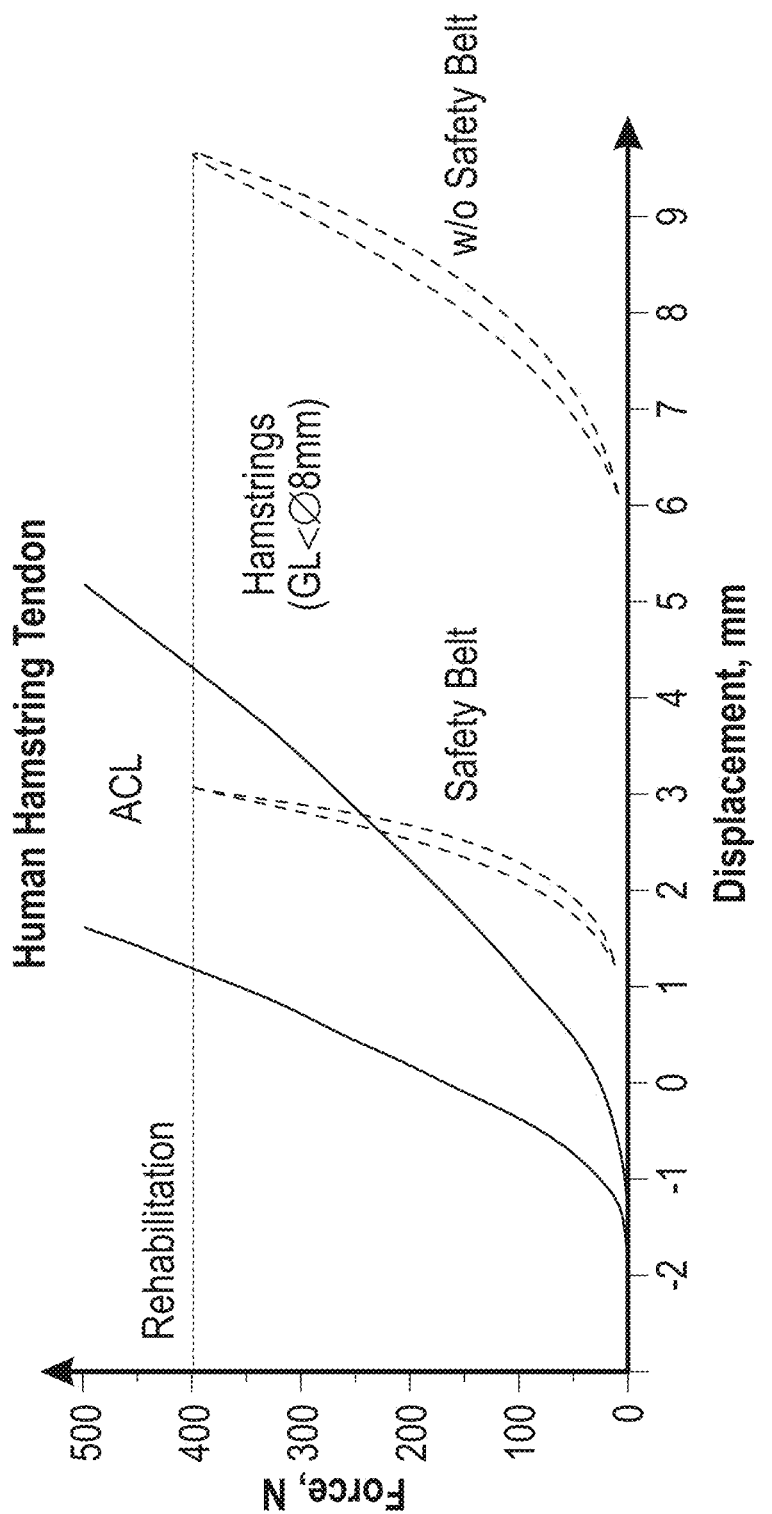
FIGS. 34, 35, 36, 37, and 38 schematically illustrate testing of a surgical fixation system that includes a human hamstring tendon graft.
Figure 35:
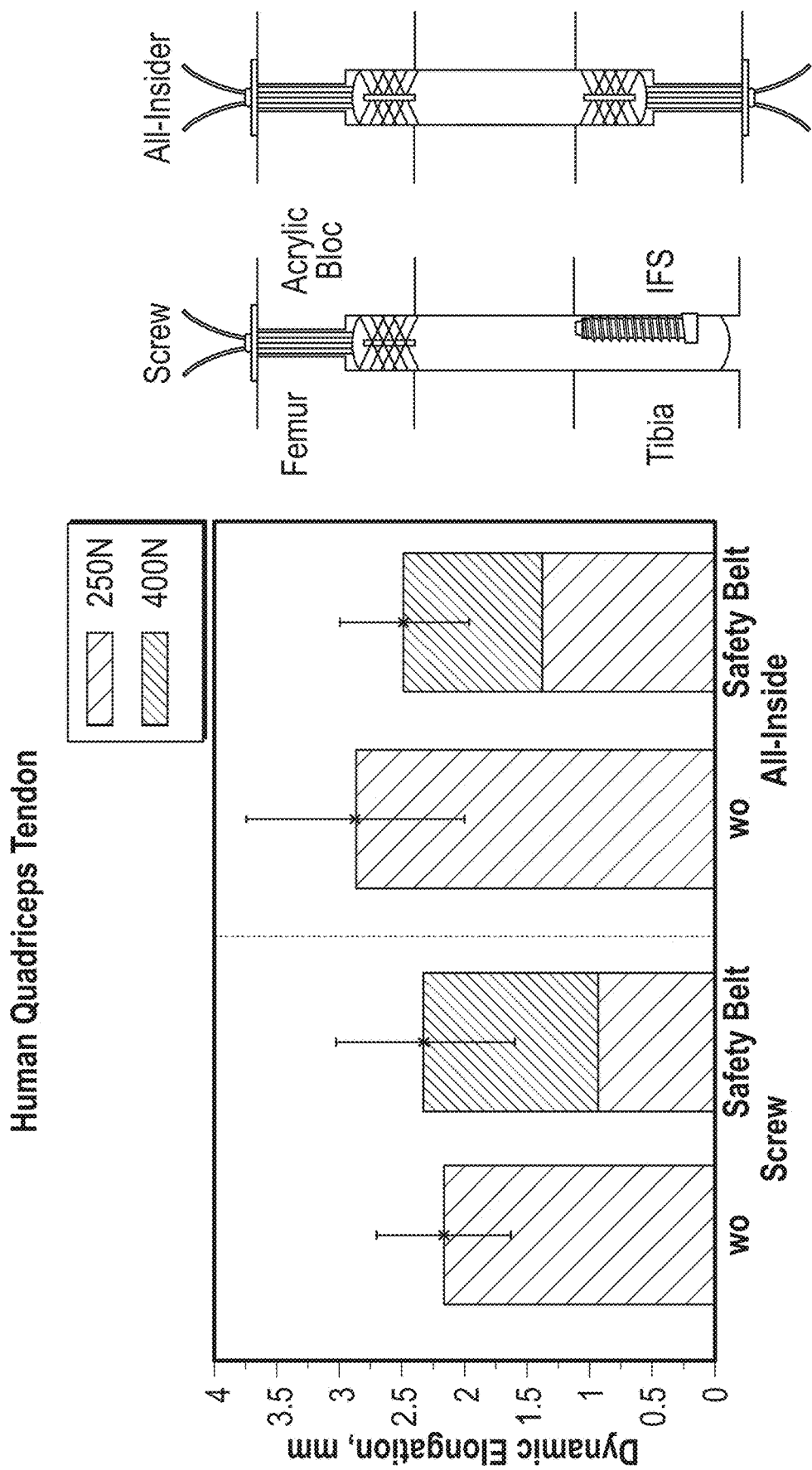
Figure 36:
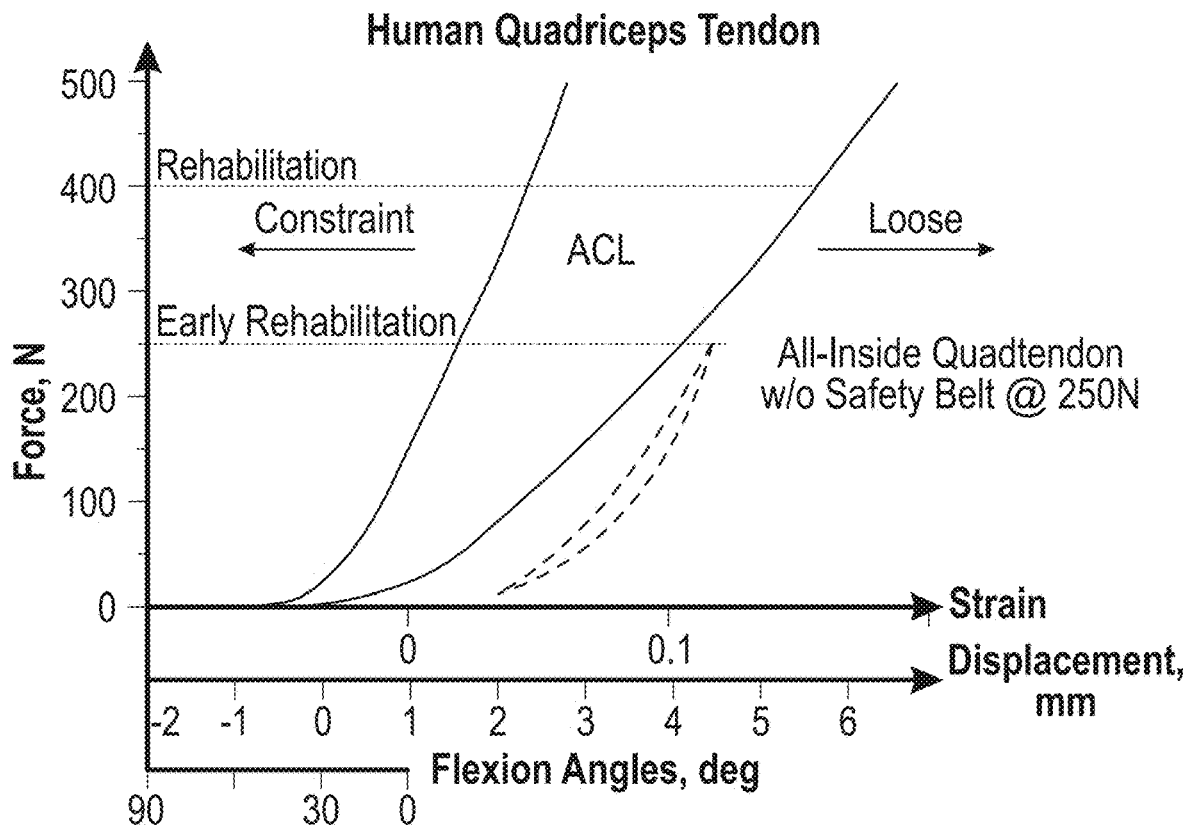
Figure 36:
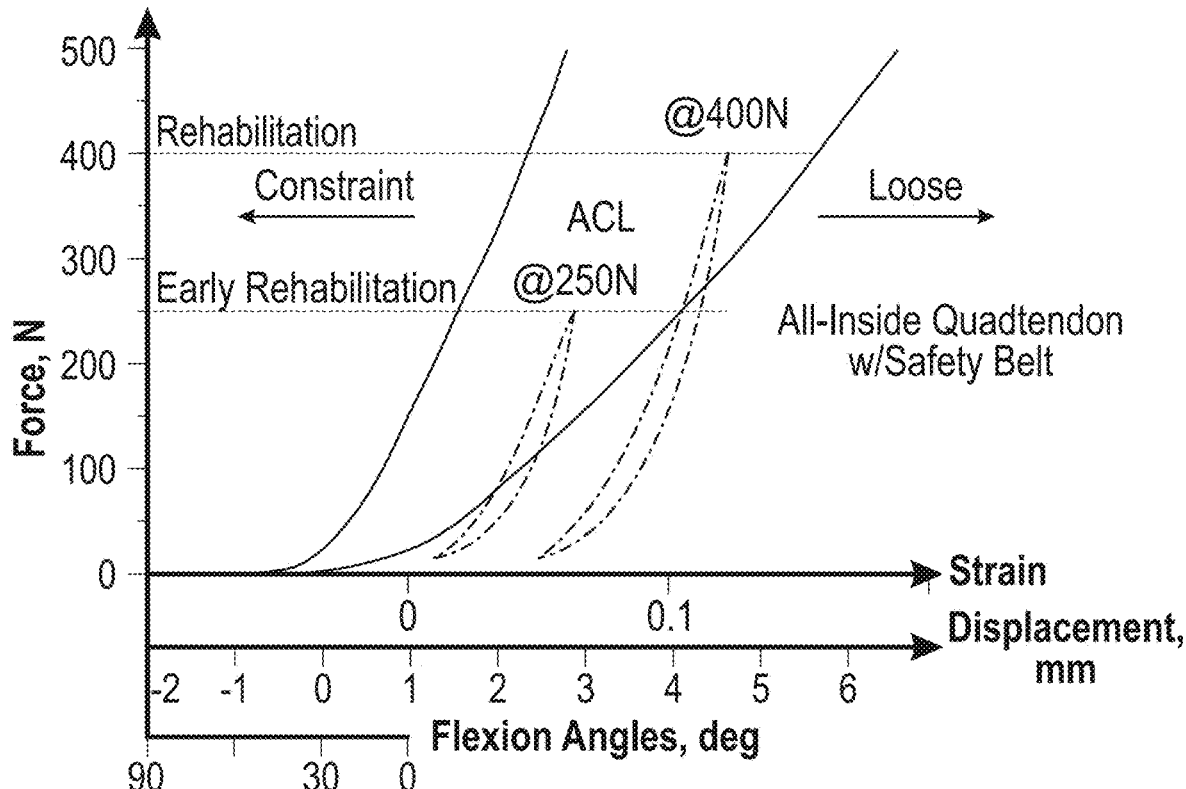
Figure 37:
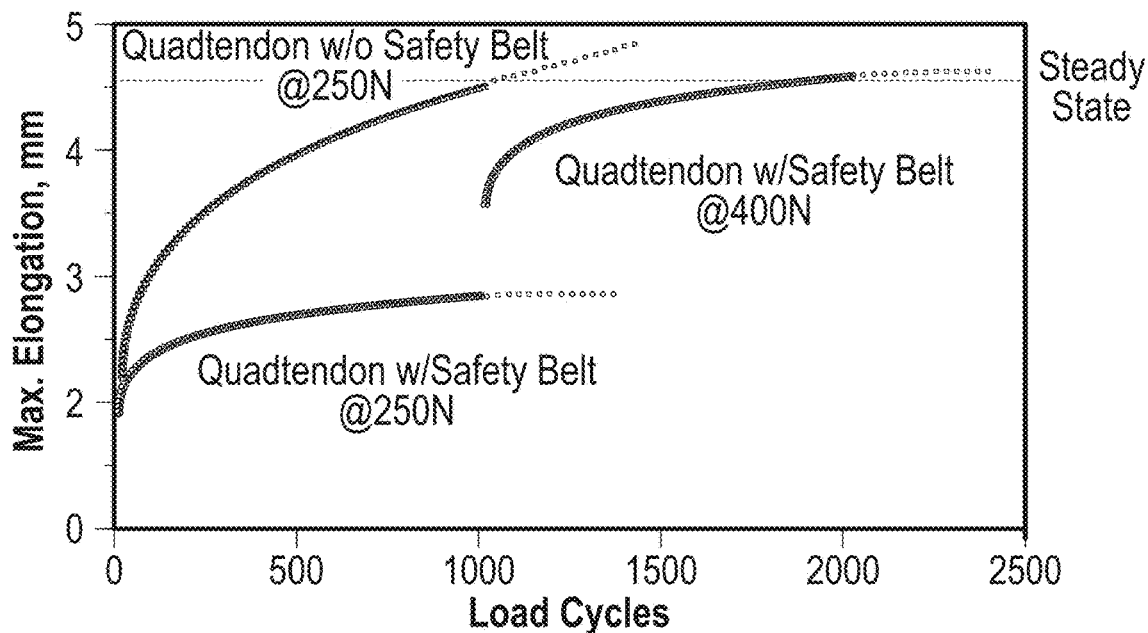
Figure 38:
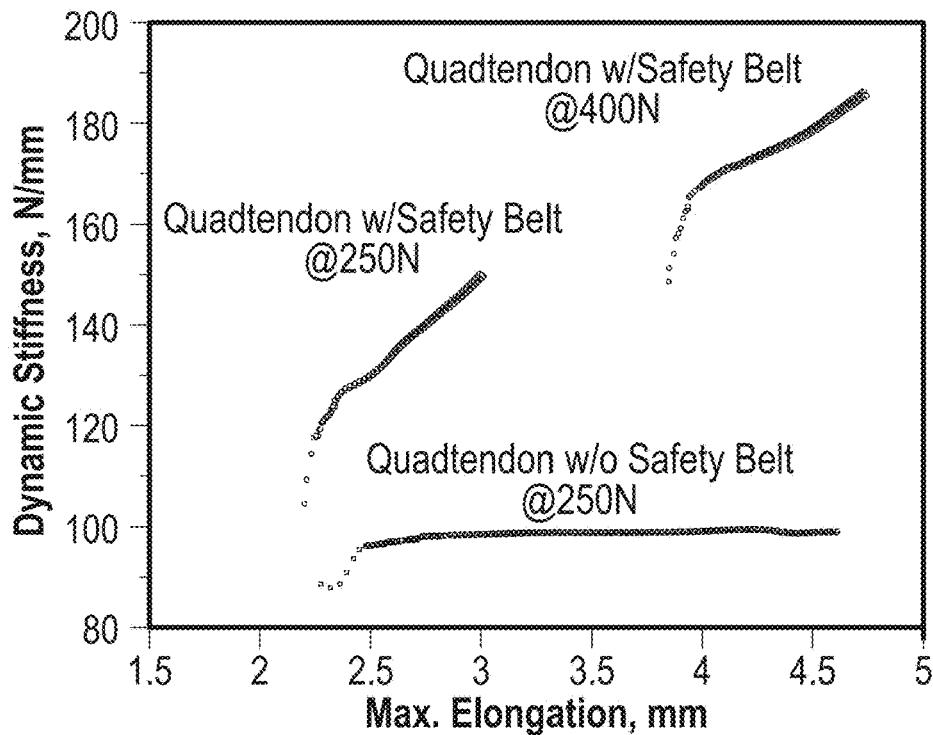

A surgical fixation system similar to the system 210 of FIG. 21 was tested using a bovine tendon graft. The testing included measuring displacement (FIG. 29), elongation (FIG. 30), stiffness versus elongation (FIG. 31), force versus displacement (FIG. 32), and pull to failure forces (FIG. 33).

Example 14: Human Hamstring Graft

A surgical fixation system similar to the system 210 of FIG. 21 was tested using a human hamstring tendon. The results of this testing are shown in FIGS. 34-38.

Example 15: BTB Graft

Figure 39:
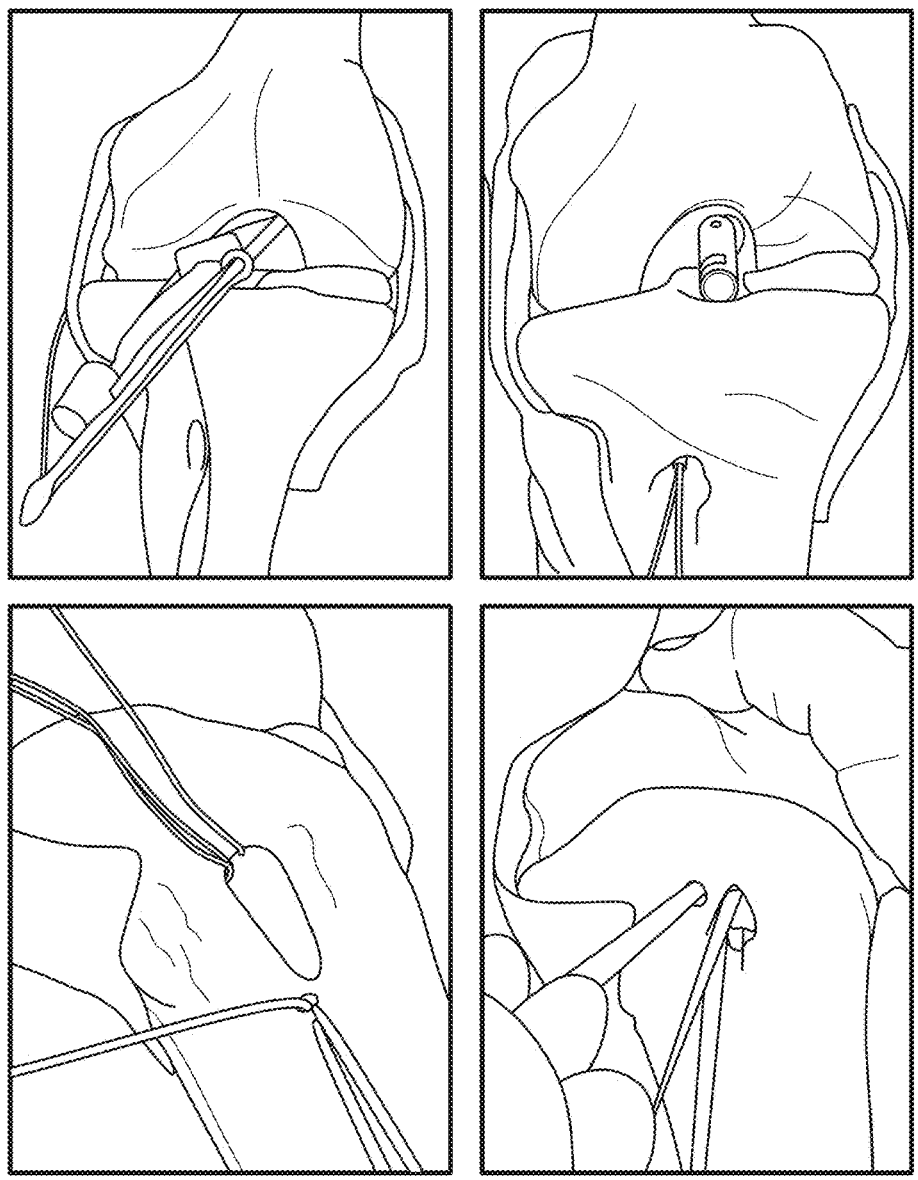
FIGS. 39, 40, and 41 schematically illustrate testing of a surgical fixation system that includes a bone tendon bone (BTB) graft.
Figure 40:
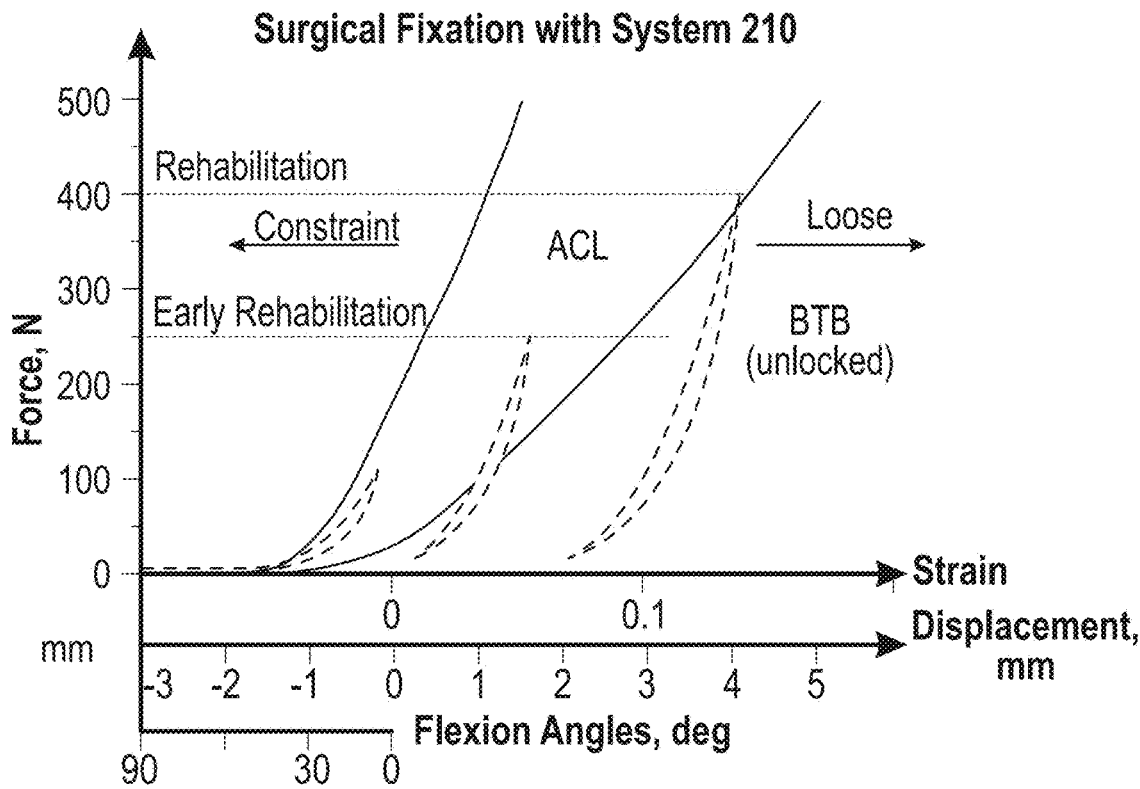
Figure 41:
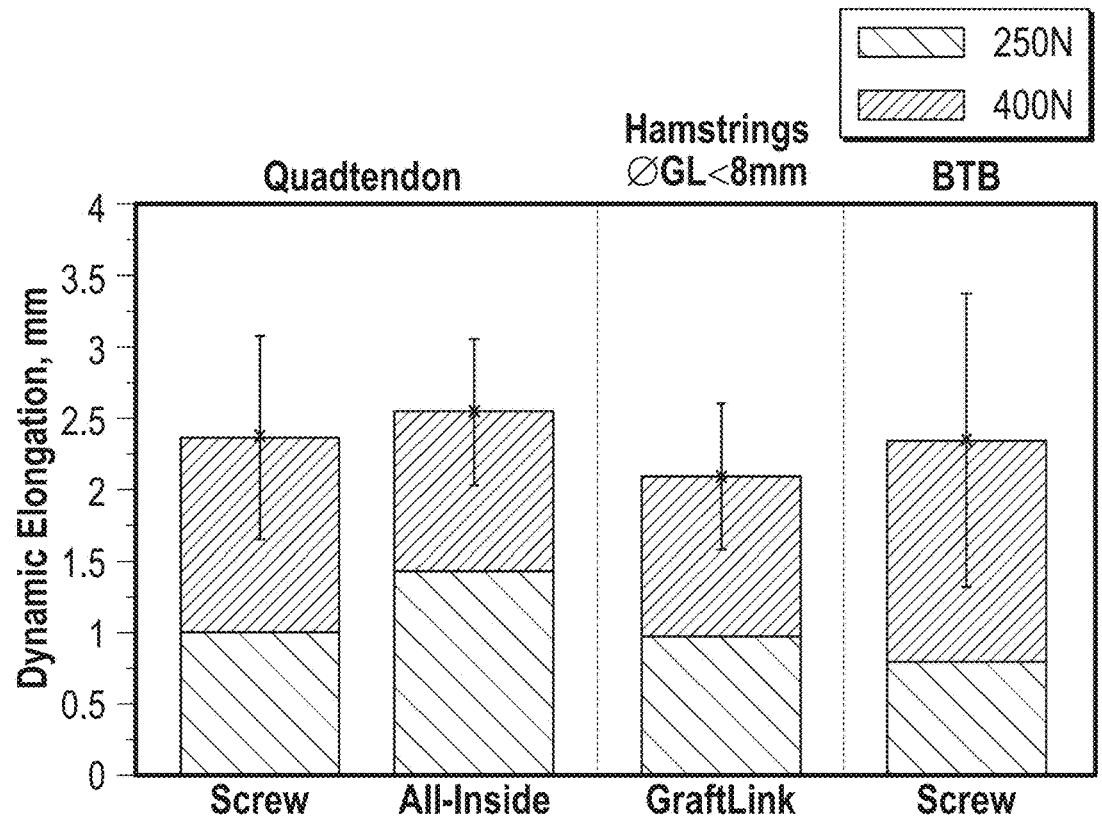

A surgical fixation system similar to the system 210 of FIG. 21 was tested using a bone tendon bone graft. The procedure and testing results for this example are shown in FIGS. 39-41.

The surgical fixation systems described above provide an adjustable fixation system for reinforcing and augmenting graft fixation within a bone tunnel. Separation of the fixation points of the graft and the reinforcement material of the system allows for independent tensioning of the graft and the reinforcement material, prevents stress shielding of the graft, and increases the ultimate failure load of the system.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A surgical fixation system, comprising:
    a button;
    a loop connected to the button; and
    a reinforcement material connected to the button and tensionable separately from the loop,
    wherein the reinforcement material is received through a first aperture and a second aperture of the button.

2. The surgical fixation system as recited in claim 1, comprising a graft received over a portion of the loop.

3. The surgical fixation system as recited in claim 2, wherein the reinforcement material is unattached to the graft and is tensionable separately from the graft.

4. The surgical fixation system as recited in claim 2, wherein the graft is looped over a cradle of the loop.

5. The surgical fixation system as recited in claim 1, wherein the loop is an adjustable loop that includes at least one adjustable eyesplice.

6. The surgical fixation system as recited in claim 5, wherein the adjustable loop includes a first adjustable eyesplice and a second adjustable eyesplice interconnected with the first adjustable eyesplice.

7. The surgical fixation system as recited in claim 1, wherein the reinforcement material includes a biological construct or a superelastic material.

8. The surgical fixation system as recited in claim 1, wherein the reinforcement material includes a suture tape.

9. The surgical fixation system as recited in claim 1, wherein the loop includes a free braid strand that is configured to reduce a size of the loop.

10. The surgical fixation system as recited in claim 9, wherein the free braid strand extends through at least one of the first aperture or the second aperture of the button.

11. The surgical fixation system as recited in claim 1, comprising a second button and a second loop connected to the second button, wherein the reinforcement material is connected to the second button.

12. The surgical fixation system as recited in claim 1, comprising a passing suture passed through the button.

13. The surgical fixation system as recited in claim 1, wherein the reinforcement material includes a suture tape, and the loop includes a spliced suture.

14. The surgical fixation system as recited in claim 1, comprising a graft connected to the loop, wherein the graft includes tissue, tendon, ligament, synthetic material, biologic material, bone, or any combination of tissue, tendon, ligament, synthetic material, biologic material and bone.

15. The surgical fixation system as recited in claim 1, wherein the reinforcement material is tensionable separately from the loop when the surgical fixation system is implanted within a bone.

16. The surgical fixation system as recited in claim 1, wherein the reinforcement material passes through the first aperture, across a section of the button disposed between the first aperture and the second aperture, and through the second aperture.

17. A surgical fixation system, comprising:
a button;
a loop connected to the button;
a reinforcement suture connected to the button and tensionable separately from the loop,
wherein the reinforcement suture is looped through both a first aperture and a second aperture of the button; and
a screw or a suture anchor configured for attaching a portion of the reinforcement suture.

18. The surgical fixation system as recited in claim 17, wherein the reinforcement suture passes through the first aperture, across a section of the button disposed between the first aperture and the second aperture, and through the second aperture.

19. A surgical fixation system, comprising:
a button;
a loop connected to the button;
a reinforcement suture connected directly to the button and tensionable separately from the loop,
wherein the reinforcement suture is accommodated within at least one of a first aperture or a second aperture of the button;
a passing suture connected to the button; and
a flipping suture connected to the button.

20. The surgical fixation system as recited in claim 19, wherein a portion of the reinforcement suture passes directly through the first aperture or the second aperture such that the first aperture or the second aperture circumscribes the portion.

* * * * *